(12) United States Patent
Contreras et al.

(10) Patent No.: US 7,244,619 B2
(45) Date of Patent: *Jul. 17, 2007

(54) SERUM MARKER FOR MEASURING LIVER FIBROSIS

(75) Inventors: Roland Henry Contreras, Merelbeke (BE); Nico L.M. Callewaert, Lichtervelde (BE)

(73) Assignees: VIB VZW, Zwijnaarde (BE); Universiteit Gent, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/180,867

(22) Filed: Jul. 13, 2005

(65) Prior Publication Data

US 2006/0014294 A1    Jan. 19, 2006

Related U.S. Application Data

(63) Continuation of application No. PCT/EP2004/050018, filed on Jan. 14, 2004.

(30) Foreign Application Priority Data

Jan. 14, 2003 (EP) .................................. 03100058
Dec. 11, 2003 (EP) .................................. 03104651

(51) Int. Cl.
    *G01N 33/00* (2006.01)
    *C08B 37/00* (2006.01)
(52) U.S. Cl. ........................ 436/94; 436/63; 436/93; 536/53
(58) Field of Classification Search .................. 436/63, 436/93–95; 435/7.1; 536/53
    See application file for complete search history.

(56) References Cited

U.S. PATENT DOCUMENTS 5,831,037 A    11/1998    Ohsuga et al.

6,631,330 B1    10/2003    Poynard
2004/0039553 A1    2/2004    Poynard

FOREIGN PATENT DOCUMENTS

| EP | 0 698 793 | 2/1996 |
| WO | WO 03/087833 | 10/2003 |
| WO | WO 2004/063753 | 7/2004 |

OTHER PUBLICATIONS

PCT International Search Report, PCT/EP2004/050018, dated Jul. 2, 2004.
PCT International Preliminary Examination Report, PCT/EP2004/050018, dated Jul. 2, 2004.
Miyamoto et al., "Characteristics of Lectin Staining Patterns Assessed by a Modified Sensitive Thermo-Method in Rat Livers with Heterologous Serum-Induced Fibrosis," Journal of Veterinary Medical Science, Aug. 1998, pp. 953-960, vol. 60, No. 60.
Gebo et al., "Role of Liver Biopsy in Management of Chronic Hepatitis C: A Systematic Review," Hepatology, Nov. 2002, pp. S161-S172, vol. 36, No. 5.
Matsumoto et al., "Alteration of asparagine-linked glycoslation in serum transferrin of patients with hepatocellular carcinoma," Clinica Chimica Acta, 1994, pp. 1-8, vol. 224.
Imbert-Bismut F. et al. Biochemical markers of liver fibrosis in patients with hepatitis C virus infection: a prospective study. *Lancet* 357, 1069-1075 (2001).
Poynard T. et al. Biochemical markers of liver fibrosis in patients infected by hepatitis C virus: longitudinal validation in a randomized trial. *J. Viral. Hepat.* 9, 128-133 (2002).

*Primary Examiner*—Maureen M. Wallenhorst
(74) *Attorney, Agent, or Firm*—TraskBritt

(57) ABSTRACT

The invention provides methods and kits to detect liver fibrosis or a change in the gradation of liver fibrosis in mammals. The diagnostic marker is based on the profiling and identification of diagnostic carbohydrates present in a body fluid such as blood serum.

12 Claims, 9 Drawing Sheets

SERUM MARKER FOR MEASURING LIVER FIBROSIS

CROSS-REFERENCE TO RELATED APPLICATIONS

This application is a continuation of PCT International Patent Application No. PCT/EP2004/050018, filed on Jan. 14, 2004, designating the United States of America, and published, in English, as PCT International Publication No. WO 2004/063753 A2 on Jul. 29, 2004, which application claims priority to European Patent Application No. 03104651.9, filed Dec. 11, 2003, which in turn claims priority to European Patent Application No. 03100058.1 filed Jan. 14, 2003, the contents of the entirety of each of which are incorporated by this reference.

TECHNICAL FIELD

The invention relates generally to medicine and biotechnology, and provides, among other things, methods and kits to detect liver fibrosis or a change in the gradation of liver fibrosis in mammals. The diagnostic marker is based on the profiling and identification of diagnostic carbohydrates present in a body fluid such as blood serum.

BACKGROUND

Liver fibrosis is characterized by the deposition of collagen and other extracellular matrix proteins and their organization in complex polymers, which are insoluble and induce loss of the liver architecture. Collagen and matrix proteins that constitute fibrosis are largely produced by activated hepatic stellate cells. The stellate cells are activated from a quiescent lipocyte phenotype to a fibroblastic phenotype. The activation occurs in two phases: initially, activation of stellate cells by cytokines (especially TGF-beta), chemokines and other signaling molecules induced by the inflammatory process, followed by transformation of the stellate cells into a myofibroblastic phenotype, in which the cell can proliferate, attract leukocytes and produce extracellular collagen and matrix proteins. In all forms of chronic hepatitis, active fibrosis begins around the portal areas (periportal zone or zone 1 fibrosis, Metavir fibrosis stage 1) and gradually extends out into the lobules towards the central veins (zone 3), with septa formation (Metavir fibrosis stage 2). Then, bridging occurs (Metavir fibrosis stage 3). The final stage of fibrosis (Metavir fibrosis stage 4) is early cirrhosis: extensive fibrosis linking portal and central areas, accompanied with nodular regeneration of the liver parenchyma. Other histological scores, apart from the Metavir system, are also often used, such as the HAI score. The HAI score distinguishes no fibrosis (grade 0) from mild, non-bridging fibrosis (grade 1); bridging fibrosis (grade 3) and early cirrhosis (grade 4). Liver fibrosis accompanies most chronic liver disorders and is characterized by the growth of scar tissue between areas of functional liver tissue. As such, growth of connective tissue is a normal reaction to tissue injury, but it can "overshoot," resulting in liver fibrosis. The rate of progression of fibrosis is the disease-defining hallmark of chronic hepatic diseases, as it is this fibrosis progression that ultimately leads to architectural distortion of the liver, and to cirrhosis. It is important to assess the stage of fibrosis and the rate of progression of fibrosis, as some chronic liver disease patients progress rapidly, finally ending up with cirrhosis and the associated life-threatening complications, whereas others progress very slowly, if at all, and might never suffer from liver-associated complications. Therefore, liver biopsy is generally performed in newly diagnosed chronic liver patients. However, this is an invasive, often painful diagnostic technique that sometimes is accompanied with serious complications. Moreover, although it is considered to be the "gold standard" for fibrosis staging, liver biopsy might under-sample the true state of the liver disease, as only a small area is probed. Thus liver biopsy is not well suited as a routine follow-up tool. An ideal tool for the follow-up of liver fibrosis would be a non-invasive clinical bio-marker, the measured values of which should correlate with the fibrosis stage (the gradation of liver fibrosis). Several markers and marker sets have been evaluated towards this goal, but none of them fully satisfies these requirements. For example, extracellular matrix components present in serum have been used, with serum hyaluronic acid apparently being the most reliable one. Still, the consensus that seems to arise from the accumulating studies that involve this marker, is that it can be quite reliable to exclude cirrhosis in a number of patients (high negative predictive value), although its accuracy in cirrhosis detection is low (about 30% sensitivity). Binary logistic regression models such as "Fibrotest", based on a range of clinical chemistry analytes have recently been much studied for these purposes (ref. 14, 15 and PCT International Patent Publication WO 0216949, the contents of the entirety of which is incorporated herein by this reference). However, these markers have a low sensitivity at the >95% specificity levels that would be required to obviate the need for biopsy in chronic liver disease patients, or to reliably detect the onset of early cirrhosis in a follow-up setting. It is clear that additional serum markers with high specificity and good sensitivity are needed for non-invasive monitoring of liver fibrosis and its progression. In the present invention, we have developed a "clinical glycomics" method that uses a standard PCR thermocycler and an automated DNA sequencer/fragment analyzer to rapidly generate high-resolution profiles of the N-glycan post-translational modifications present on the proteins in patient's serum. We show that the serum N-glycome yields a biomarker that distinguishes early cirrhotic from fibrotic liver disease patients with 79% sensitivity and 86% specificity. Importantly, when our new biomarker is used together with the clinical chemistry-based {Fibrotest} biomarker (which detects early cirrhosis in our invention with 92% sensitivity and 76% specificity), the specificity for the differentiation between fibrosis and early cirrhosis cases improved to 100%, while retaining a sensitivity of 75%.

BRIEF SUMMARY OF THE INVENTION

Currently, the diagnostic work-up of first-presentation patients with a chronic liver disorder calls for a liver biopsy to assess fibrosis stage and activity, and to detect the onset of early cirrhosis.[10] However, in a large subgroup of the chronic liver disease patients (mainly chronic viral hepatitis, genetically caused or alcohol-abuse related liver disorders), fibrosis progresses with variable rates to cirrhosis, a development which finally leads to severe complications[11] and significant mortality and which is a major risk factor for the development of hepatocellular carcinoma[12] (HCC). As liver biopsy is a procedure with significant discomfort to the patient and with some risk for complications,[13] it is not suitable to incorporate it in the routine (generally yearly) follow-up of chronic liver disease patients. Therefore, there is a clinical demand for markers that could routinely assess the progression of the liver fibrosis, and could reliably detect the stage of early liver cirrhosis, which is associated with the most significant morbidity.

In the present invention, we satisfy this need and we have developed a technology platform for a clinical glycomics application in the detection of liver fibrosis and a detection in the change of the gradation of liver fibrosis in a patient previously diagnosed with liver fibrosis. We have quantitatively profiled the carbohydrate structures derived from the glycoproteins present in serum and have identified statistically relevant correlations between quantitative parameters derived from these parameters and the histological liver fibrosis stage of the patients under study. In other words, amounts of diagnostic carbohydrates or relative amounts between carbohydrates have surprisingly been identified in the present invention that are correlated with the severity of liver fibrosis.

In a first embodiment, the invention provides a method to detect liver fibrosis or a change in the gradation of liver fibrosis in a mammal, comprising (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; the carbohydrates or the fragments being present on a mixture of glycoconjugates or obtained from a mixture of glycoconjugates that are present in or are isolated from a sample of a body fluid from the mammal, and (b) measuring in the profile of step a) the amount of at least one carbohydrate or a fragment derived thereof or a labeled derivative of the carbohydrate or the fragment, or a feature of at least one carbohydrate or fragment derived thereof present in the carbohydrate profile, and (c) comparing the measured data obtained in step b) with measured data obtained from profiles derived from mammals free of liver fibrosis in order to detect liver fibrosis or, comparing the data obtained in step b) with previously measured data in the mammal in order to detect a change in the gradation of liver fibrosis and (d) attributing the results of the comparison obtained in step c) to detect liver fibrosis or a change in the gradation of liver fibrosis in a mammal.

DETAILED DESCRIPTION OF THE INVENTION

Figure 1:
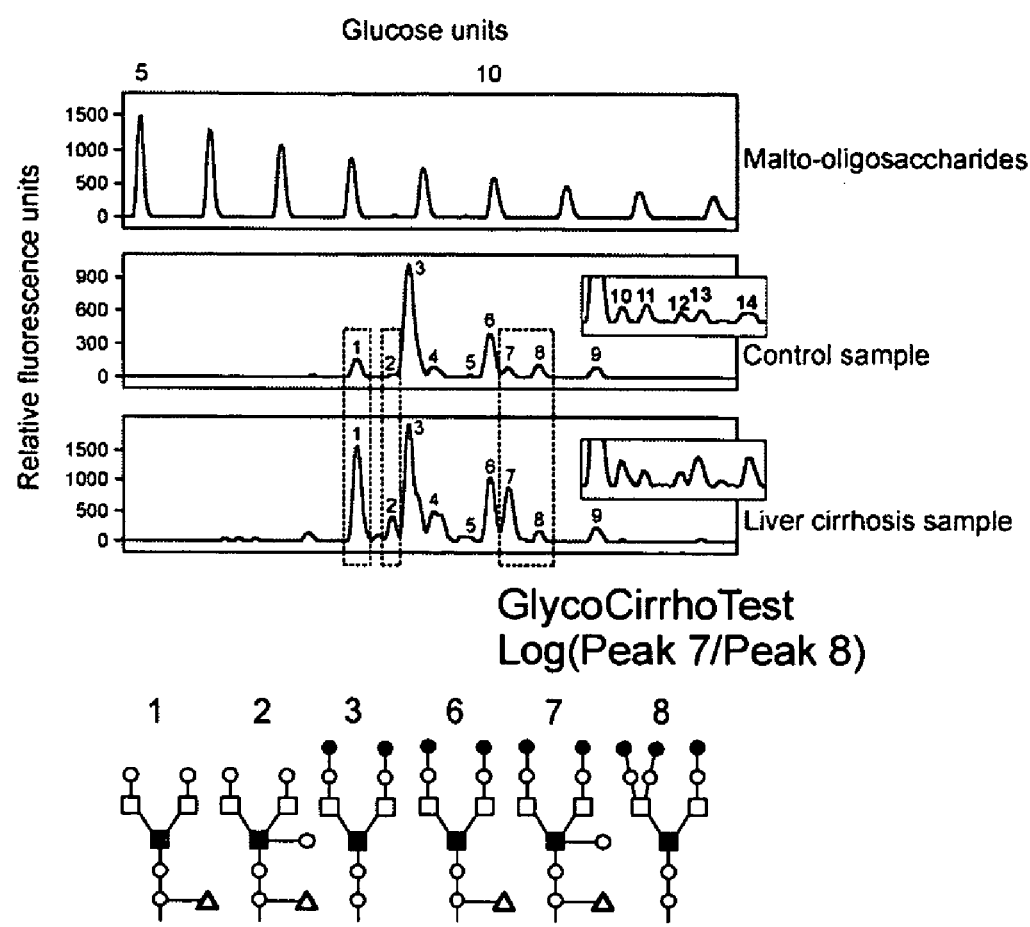
FIG. 1: Total serum protein N-glycan profile examples. The upper panel contains a malto-oligosaccharide reference. The second panel shows a typical electropherogram of the desialylated N-glycans derived from the proteins in a control serum sample. Nine peaks are clearly visible in the full detection range, five more in the 10× blow-up of the latter part of the electropherogram. The height of these 14 peaks was used to obtain a numerical description of the profiles of all samples in this study. The third panel shows a representative electropherogram obtained from a cirrhosis case. The structures of the N-glycans that are of relevance to this study are shown below the panels, and the peaks that were found to be of particular relevance for the cirrhosis markers are boxed. Monosaccharide unit symbols (also valid for FIG. 5): ○β-linked GlcNAc; ○β-linked Gal; □α-linked Man; □β-linked Man; Δα-1,6-linked Fuc.

The wording "a method to detect liver fibrosis" can be broadly understood as a method for screening, a method for diagnosis or a method for prognosing (or monitoring) liver fibrosis. The wording "a change in the gradation of liver fibrosis" refers to the evolution of liver fibrosis over time which can mean an improvement of the stage of liver cirrhosis (e.g., from Metavir stage 3 to Metavir stage 2) or a stabilization of the stage of liver fibrosis or a worsening of the stage of liver fibrosis. A method to detect a gradation of liver fibrosis is in other words a monitoring instrument which can be used for providing a prognosis for a patient (or patient population) previously diagnosed with liver fibrosis. In the wording "attributing the results of the comparison" refers to the different forms of results that can be obtained. "Results" can comprise an increase in a value, a decrease in a value, a stability in a value. Alternatively "results" can fall within a range of values (e.g., 95% confidence interval, a standard deviation) obtained from, for example, an analysis of groups of patients with a histologically confirmed specific stage of fibrosis. In the present invention, Metavir stage 4 (IV) refers to early cirrhosis or late stage fibrosis meaning that the wording early cirrhosis or late stage fibrosis or equivalent. Also the wording "pre-cirrhotic" refers here to fibrotic stages 1, or 2, or 3.

In another embodiment, a carbohydrate profile is used for the manufacture of a diagnostic assay for the detection of liver fibrosis, the diagnostic assay comprises the following steps: (a) generating a profile of carbohydrates or fragments derived thereof, or labeled derivatives of the carbohydrates or the fragments, or features of the carbohydrates or the carbohydrate fragments that are determined by the structure of the carbohydrates or the carbohydrate fragments; the carbohydrates or the fragments being present on a mixture of glycoconjugates or obtained from a mixture of glycoconjugates that are present in or are isolated from a sample of a body fluid from the mammal, and (b) measuring in the profile of step a) the amount of at least one carbohydrate or a fragment derived thereof or a labeled derivative of the carbohydrate or the fragment, or a feature of at least one carbohydrate or fragment derived thereof present in the carbohydrate profile, and (c) comparing the measured data obtained in step b) with measured data obtained from profiles derived from mammals free of liver fibrosis in order to detect liver fibrosis or, comparing the data obtained in step b) with previously measured data in the mammal in order to detect a change in the gradation of liver fibrosis and (d) attributing the results of the comparison obtained in step c) to detect liver fibrosis or a change in the gradation of liver fibrosis in a mammal.

The wording "glycoconjugates that are present in" refers to carbohydrates which are detected on the glycoconjugates without any isolation step of the carbohydrates; thus the sample is used as such and does not imply any isolation step of the carbohydrates, whereas the wording "are isolated from a sample of a body fluid" refers to the fact that the carbohydrates are isolated from the glycoconjugates present in the sample.

In a particular embodiment, the method of the invention can be used for monitoring the effect of therapy administered to a mammal suffering from liver fibrosis. In another particular embodiment, the method of the invention specifically detects liver fibrosis. The term "specifically" refers to the fact that liver fibrosis can be diagnosed differently from other hepatic disorders comprising early liver cirrhosis and late stage liver cirrhosis.

The term "carbohydrate" can be understood as glycans that are present in the structure of glycoconjugates or that are derived from glycoconjugates, comprising the glycan categories known in the art as asparagine-linked glycans (also designated as N-glycans) or Serine/Threonine-linked glycans (also designated as O-glycans) of proteins or glycosaminoglycans or proteoglycan derived glycans, glycans present in or derived from glycolipids and GPI-anchor derived carbohydrates. In a preferred embodiment, the carbohydrates are N-glycans. The words "glycan" and "carbohydrate" are interchangeable. A "glycoconjugate" means any compound (e.g., protein or lipid) containing a carbohydrate moiety.

With the wording "a mixture of glycoconjugates," it is meant a composition containing at least two (at least three, at least four, at least five or more) of the glycoconjugates, potentially also comprising non-glycoconjugate materials, such as proteins, lipids, salts and water. The wording "carbohydrates or fragments derived thereof" means that carbohydrates can be fragmented to yield at least one oligosaccharide or a derivative thereof amongst the products of the fragmentation process. Other products of this fragmentation process might include monosaccharides and oligosaccharides or derivatives thereof. An oligosaccharide is a carbohydrate of which the chemical structure consists of at least two chemically linked units known in the art as monosaccharide. The fragmentation process can involve enzymatic, chemical and physical treatments. For example, carbohydrates can be treated (or digested) with a glycosidase enzyme (e.g., a sialidase to remove the sialic acid residues from the carbohydrates, or a fucosidase to remove fucose residues from the carbohydrates) and, therefore, the profile obtained consists of fragments of the carbohydrates. Glycosidase digestions can, for example, be carried out to obtain a more simple profile of the carbohydrates.

Sialic acids may also be removed in a chemical way by mild acid hydrolysis of the carbohydrates. In mass spectrometric analysis methods, the word "fragments" refers to the fact that carbohydrates are very often fragmented in the process of analysis (for example, in collision induced dissociation), in which case the fragmentation products can also yield an oligosaccharide derivative made up of an oligosaccharide chemically linked to the remnant of one or more monosaccharides that were part of the structure of the carbohydrate before fragmentation took place. An example of such an oligosaccharide derivative being the product of a mass spectrometric fragmentation process is known in the art as a cross-ring cleavage product ion. A "feature of the carbohydrate" refers to any measurable parameter of which the properties and/or the quantity is determined by the structure of the carbohydrate. Examples of such measurable parameters are, for example, nuclear magnetic resonance parameters, such as chemical shifts, homonuclear and heteronuclear coupling constants, Nuclear Overhauser Effects and residual dipolar couplings. Alternatively, such measurable parameters might be the extent of binding to the carbohydrate to other molecules, such as lectins and antibodies that recognize specific structural determinants or combinations thereof in the carbohydrate. Yet other such measurable parameters might be the extent of the capacity of the carbohydrate to function as a substrate for an enzyme that specifically modifies certain carbohydrates, such as glycosyltransferases and glycosidases.

The wording "the carbohydrates or the fragments being present on a mixture of glycoconjugates or obtained from a mixture of glycoconjugates" refers to the fact that a "profile of carbohydrates or fragments derived thereof or labeled derivatives of the carbohydrates or the fragments, or features of the carbohydrates or the carbohydrate fragments that are determined by the structure of the carbohydrates or the carbohydrate fragments" can be either obtained from carbohydrates that are still chemically linked to the glycoconjugates in the mixture, or from carbohydrates that have been released (isolated) from the glycoconjugates by enzymatic, chemical or physical means.

In a preferred embodiment, N-glycans are released from the glycoproteins in the mixture by enzymatic digestion with Peptide N-glycosidase F or other endoglycosidases known in the art.

In another embodiment, N-and O-glycans can be released using a procedure involving hydrazine, known to those skilled in the art.

In yet another embodiment, O-glycans can be selectively released using beta elimination in alkaline conditions according to well-known procedures. In case the profile is obtained on carbohydrates that are still chemically linked to the glycoconjugates in the mixture, one embodiment involves the use of enzymes or chemical procedures to modify the non-glycan part of the glycoconjugate prior to obtaining the profile, such as proteases or enzymes which modify the lipid part of glycolipids. The wording "a profile of carbohydrates" means any entity comprising qualitative and/or quantitative information on the carbohydrates. For example, this may mean an electrophoretic or chromatographic profile of the carbohydrates. In a particular case the profile is a mass spectrum of the carbohydrates. Alternatively, the profile can be information obtained by Nuclear Magnetic Resonance analysis. In yet another example, the profile can be information describing qualitative or quantitative aspects of lectin binding to the carbohydrates. Alternatively, the profile can be information describing the extent to which the carbohydrates are substrates for specific enzymes, such as glycosyltransferases or glycosidases. Such information can include read-outs of measurements of by-products of such enzymatic reactions, such as nucleotides set free in equimolar amounts in glycosyltransferase reactions.

In a particular embodiment, the wording "generating a profile of carbohydrates" or "profiling of carbohydrates" also can imply that the glycan structures are separated and subsequently detected. Usually a number of carbohydrates are identified in a profile of carbohydrates. Usually the carbohydrates are present in a complex mixture and separation is necessary for an efficient detection. Separation can be carried out with methods comprising electrophoretic and chromatographic methods. Detection can be carried out with methods comprising antibody detection, lectin detection, NMR, mass spectrometry and fluorescence.

In a particular embodiment, it is necessary to chemically and/or enzymatically remove the glycans from the glycoproteins before the glycans can be profiled. Methods to prepare glycans from glycoproteins are well known in the art.

In another particular embodiment, it is necessary to derivatize the glycans before the separation and the detection. In one approach the method of the present invention, the profiling (includes separation and detection) of glycans can be carried out in combination with a DNA-sequencer. However, it is clear for the person skilled in the art that this method can also be applied in connection with capillary electrophoresis systems adaptable to a laser induced fluorescence detector. Such systems for instance include the P/ACE series Capillary Electrophoresis Systems (Beckman Instruments, Inc., Fullerton, Calif.). The invention can also be applied with any electrophoresis system which is adaptable with a laser induced fluorescence detector.

In another embodiment, mass spectrometric detection methods can also be used, such as MALDI-TOF-MS for the measurement of the amount of at least one carbohydrate or a fragment derived thereof. In mass spectrometric methods, very often the carbohydrates are fragmented and, therefore, in the methods, fragments of carbohydrates are detected.

In yet another embodiment, the profiling can be carried out with a microfluidics method. Microfluidics is a rapidly growing field and is based on fluid migration through narrow-bore channels created in a solid medium (mostly silica wafers or high-purity glass plates) via techniques borrowed from the microchip industry (photolithography and chemical wet etching). Fluids can migrate through these channels via capillary action or active pumping, and analytes can migrate in fluid-filled channels through electrophoresis (Schmalzing et al. (2001) *Methods Mol. Biol.* 163, 163-173).

In yet another embodiment, the separation of carbohydrates can be carried out via a chromatographic separation with methods including thin layer chromatography (TLC), high performance liquid chromatography or gas chromatography.

The term "at least one carbohydrate" refers to the measurement of the amount of at least one carbohydrate present in the carbohydrate profile that is diagnostically relevant for the detection of liver fibrosis (at least one carbohydrate can, therefore, be designated as an at least one diagnostic carbohydrate).

In one embodiment, the measurement of one carbohydrate is sufficient to diagnose liver fibrosis. This means that in one particular case one carbohydrate is present in a mammal suffering from fibrosis and is absent in a mammal free of fibrosis, in another particular case one carbohydrate is present in a mammal free of fibrosis and absent in a mammal suffering from fibrosis. In another particular example, a different amount of one carbohydrate is sufficient to differentiate between a mammal suffering from fibrosis and a mammal free of fibrosis.

In a preferred embodiment, the amount of one, two or even more (diagnostic) carbohydrates is measured. In a profiling method the amount of the (diagnostic) carbohydrate can, for example, be measured by calculating the peak height or the peak surface. By comparing the amount of at least one (diagnostic) carbohydrate, present in patient samples, with corresponding diagnostic carbohydrate levels present in an individual free of liver fibrosis, the presence or absence of liver fibrosis can be diagnosed. The invention can be used on samples obtained from mammals such as humans. Diagnostic carbohydrates may be oligosaccharides, or polysaccharides. Diagnostic carbohydrates may be branched or unbranched. Diagnostic carbohydrates in a sample from an afflicted individual with liver fibrosis are present with an abundance (amount) that is either consistently higher or consistently lower than in a sample from an unafflicted individual (not having liver fibrosis).

The term "labeled derivatives of the carbohydrates or the fragments" refers to carbohydrates that have been labeled with an agent that leads to an efficient detection of the carbohydrates. The labeled carbohydrates are also called derivatized carbohydrates. As an example, a fluorescing compound can be used for the labeling of the carbohydrates. The fluorescing compounds are also preferentially charged such that the derivatized compounds can migrate under electrophoretic conditions. When the fluorophore label is uncharged, it can be coupled with a charge imparting species. The fluorophore label also permits the quantitative measurement of the derivatized carbohydrates by fluorescence. Fluorescing compounds, such as 9-aminopyrene-1,4, 6-trisulfonic acid (APTS) and 8-aminonaphthalene-1,3,6-trisulfonic acid (ANTS), are particularly suitable for electrophoretic separation of derivatized carbohydrates. Other compounds for fluorescent labeling of carbohydrates include 2-aminopyridine (AP), 5-aminonaphthalene-2-sulfonate (ANA), 1-amino-4-napthalene sulfonic acid (ANSA), 1-amino-6,8-disulphonic acid (ANDA), 3-(4-carboxybenzoyl)-2-quinolinecarboxaldehyde (CBQCA), lucifer yellow, 2-aminoacridone and 4-aminobenzonitrile (ABN).

In a particular embodiment, regarding the detection of the fluorescently labeled carbohydrates, any detection method known in the art can be applied, but preferably the detection is carried out with a laser, such as a diode laser, a He/Cd laser or an argon-ion laser.

In a particular embodiment, the profile of labeled carbohydrate bands produced by the electrophoretic separation is visualized using an imaging system based on a charge-coupled device (CCD) camera. Information from the CCD camera may subsequently be stored in digital form and analyzed by various computer programs for comparing diagnostic carbohydrate patterns between individuals and between reference standards.

In another particular embodiment, the gel separated diagnostic carbohydrates may be transferred to an immobilizing membrane, i.e., blotted and then probed with various diagnostic carbohydrate-specific reagents, such as lectins or monoclonal or polyclonal antibodies specific for the diagnostic carbohydrates.

In a specific embodiment, the invention provides a method to detect liver fibrosis in a mammal comprising measuring and detecting at least one glycan structure and/or glycoconjugate that has a different abundance in samples derived from individuals with and without fibrosis by using ligands that specifically bind to at least one glycan structure and/or glycoconjugate. Ligands comprise lectins and antibodies. For example, the increased abundance of the N-glycan structures (or their conjugates) with a "bisecting GlcNAc" residue (GnT-III product) in a body fluid sample can be detected with a lectin that specifically recognizes glycans (or their conjugates) that are modified with a bisecting GlcNAc, such as the erythro-agglutinating lectin from *Phaseolus vulgaris* (E-PHA) or mutants thereof with, for example, improved specificity, or antibodies specific for thus modified glycans. Alternatively, the increased abundance of the N-glycan structures with a "bisecting GlcNAc" residue (or their conjugates) can be detected by a reduction in the binding to the N-glycans (or their conjugates) to lectins that only bind N-glycans (or their conjugates) if they are not substituted with a bisecting GlcNAc residue. An example of such a lectin is the lectin from *Canavalia ensiformis* (Con A). The observed undergalactosylation of the serum glycoprotein N-glycans can be detected by a terminal-GlcNAc binding lectin, such as the *Griffonia simplicifolia* II (GS-II) lectin. Alternatively, the undergalactosylation can be measured by a reduction in the binding of a terminal-galactose binding lectin, such as the lectin from *Erythrina crystagelli*.

In a particular embodiment, the "profile of a feature determined by the structure of the carbohydrates" is obtained by measuring the property of the carbohydrates that is constituted by being a substrate for a specific glycosyltransferase.

In a preferred embodiment, this glycosyltransferase is beta-1,4-galactosyltransferase and the carbohydrates are those present on the total mixture of serum or plasma proteins. An additional substrate for this reaction is UDP-Galactose, and the reaction yields UDP in a stoichiometric amount. Thus, the profile can be obtained by measuring the difference between the extent of galactosylation of the desialylated proteins before and after the reaction, for example, by a method involving binding of the glycoproteins to a lectin specific for terminal beta-galactose (such as the lectins known in the art derived from *Ricinus communis* and from *Erythrina crystagalli*, or the galectins, such as the one derived from *Coprinus cinereus*). Alternatively, the profile can be obtained by measuring the amount of UDP generated in the beta-1,4-galactosyltransferase reaction on the mixture of serum or plasma proteins, for example, by HPLC. The amount of UDP can also be measured using a coupled enzyme reaction with one or more enzymes known from nucleotide metabolism, such as, for example, a nucleotide diphosphatase, such as the yeast Golgi GDPase, which also shows significant hydrolytic activity towards UDP. In this latter case, the profile can be obtained by measuring either UMP or phosphate, using well-known techniques. Still another example of a measurement of UDP involves the use of supramolecular membrane pores with differential affinity for UDP-Gal and UDP, as known in the art. The profiles thus obtained can, for example, be standardized for the total amount of protein or carbohydrate present in the serum or plasma sample.

In yet another embodiment, the profile can be obtained by using the carbohydrates present on the mixture of serum or plasma proteins as substrate for both beta-1,4-galactosyltransferase and a sialyltransferase, with UDP-Galactose and CMP-N-acetylneuraminic acid as sugar donor substrates. In this embodiment, the profile can either consist of the difference in binding of a sialic-acid binding lectin (such as the lectin well known in the art derived from *Maackia amurensis* or *Sambucus nigra*) to the glycoproteins before and after the reaction, or can consist of measuring the amount of UDP and/or CMP released during the reaction, using methods known in the art.

In another embodiment, the carbohydrate profiling method can be supplemented pre-electrophoretically with one or more internal standards labeled with a chromophore or fluorophore different from the label attached to the carbohydrate analytes. The internal standard allows for accurate and reproducible determination of the electrophoretic mobilities of the derivatized carbohydrate by referencing these mobilities to the mobilities of the components in the internal standard mixture. For example, a rhodamine-labeled oligonucleotide standard Genescan™ 500 (Applied Biosystems, Foster City, Calif., USA) or a mixture of rhodamine-labeled 6-, 18-, 30-, and 42-meric oligonucleotides may be added to the derivatized glycans before profiling. Diagnostics standards may be labeled prior to the labeling of the samples for analysis; however diagnostic standards are preferably labeled concomitantly with the labeling for the standards for analysis. Furthermore, the diagnostic carbohydrates in the standards are preferably quantitated so as to provide for quantitative or qualitative comparisons with the amount of diagnostic carbohydrates in the samples for analysis.

The term "body fluid" includes blood, blood serum, blood plasma, saliva, urine, bone marrow fluid, cerebrospinal fluid, synovial fluid, lymphatic fluid, amniotic fluid, nipple aspiration fluid and the like. Preferred body fluids for analysis are those that are conveniently obtained from patients, particularly preferred body fluids include blood serum and blood plasma.

Although the present invention can be carried out without pre-treatment of the sample prior to the profiling of the (derivatized) glycans, in a particular embodiment, samples for analysis may require processing prior to the separation and quantification of the diagnostic carbohydrates. The precise method of sample processing employed may vary in accordance with a number of factors attributable to the choice of sample fluid and the identity of the diagnostic carbohydrates; these factors include: the abundance of the diagnostic carbohydrate, the concentration of background carbohydrates, the presence of interfering molecules, for example, molecules that adversely affect diagnostic carbohydrate band mobility or the fluorescent labeling of the diagnostic carbohydrates, and whether the fluorescent label has to be separated from the derivatized diagnostic carbohydrates. Suitable methods for this processing or pre-treatment of samples include: dialysis, to remove interfering molecules (e.g., salt for an efficient mass spectrometric detection); ultrafiltration, to concentrate diagnostic carbohydrates and remove interfering molecules; centrifugation, to remove interfering particulates or concentrate cells; precipitation, to remove interfering molecules, removal of albumin from the serum to enrich for glycosylated proteins and hence for lower abundance glycans, deglycosylation with a glycosidase (e.g., a sialidase digest of the glycans) to generate a more simple glycan profile; chromatography, such as affinity chromatography to remove, for example, albumin from the serum In yet another embodiment, the invention provides a method to detect liver fibrosis or a change in the gradation of liver fibrosis in a mammal, the method comprising (a) generating a profile of carbohydrates or fragments derived thereof, or labeled derivatives of the carbohydrates or the fragments, or features of the carbohydrates or the carbohydrate fragments that are determined by the structure of the carbohydrates or the carbohydrate fragments; the carbohydrates or the fragments being present on a mixture of glycoconjugates or obtained from a mixture of glycoconjugates that are present in or are derived from a sample of a body fluid from the mammal and (b) measuring the relative amount of at least one carbohydrate or a fragment derived thereof or a labeled derivative of the carbohydrate or the fragment, present in the carbohydrate profile and c) comparing the measured data obtained in step b) with measured data obtained from profiles derived from mammals free of liver fibrosis in order to detect liver fibrosis or, comparing the data obtained in step b) with previously measured data in the mammal in order to detect a change in the gradation of liver fibrosis and (d) attributing the results of the measurement in step c) to detect liver cirrhosis or a change in the gradation of liver fibrosis in a mammal.

The term "measuring the relative amount" refers to the aspect that the amount of at least one carbohydrate or fragment (e.g., one particular carbohydrate or fragment) can be measured between two profiles, one profile being derived from a mammal free of liver fibrosis and another profile derived from a mammal possibly suffering from liver fibrosis and to be diagnosed for liver fibrosis. Alternatively, the amount of one particular carbohydrate can be compared between an average reference range taken from mammals free of liver fibrosis and the measured amount of the particular carbohydrate in a mammal to be diagnosed for liver fibrosis.

In yet another embodiment, the "measuring of the relative amount" refers to measuring the relative amount of at least two carbohydrates or fragments derived thereof or labeled derivatives of the carbohydrates or the fragments, or features of the carbohydrates or the carbohydrate fragments present in one carbohydrate profile derived from a sample of a body fluid from an animal.

In another embodiment of the invention, in order to be able to measure relative amounts of the carbohydrates, diagnostic standards are included on the gels used to analyze the diagnostic carbohydrates in the subject samples; however, the information embodied by the diagnostic standard, e.g., band migration distance and intensity, may also be obtained from comparison with stored records made from diagnostic standards previously subjected to fluorophore assisted carbohydrate electrophoresis under conditions similar to the conditions to which the samples for analysis are exposed. Diagnostic standards may be both positive, i.e., corresponding to the complete carbohydrate pattern in an afflicted individual, or negative, i.e., corresponding to unafflicted individual. Diagnostic standards may have a composition similar to that of samples for analysis in that they may contain both diagnostic carbohydrates and background carbohydrates with composition similar to that found in actual samples. Diagnostic standards may be derived from samples obtained from afflicted and non-afflicted individuals. Alternatively, diagnostic standards may contain one or more diagnostic carbohydrates free of background carbohydrates.

In a particular embodiment, the diagnostic technique to measure liver fibrosis or a change in the gradation of liver fibrosis does not require an a priori detailed knowledge of the structure of the carbohydrates.

Thus in another embodiment, the invention provides a method for the detection of liver fibrosis or a change in the gradation of liver fibrosis in a mammal, the method comprising (a) generating a profile of carbohydrates or fragments derived thereof, or labeled derivatives of the carbohydrates or the fragments, or features of the carbohydrates or the carbohydrate fragments that are determined by the structure of the carbohydrates or the carbohydrate fragments; the carbohydrates or the fragments being present on a mixture of glycoconjugates or obtained from a mixture of glycoconjugates that are present in or are isolated from a sample of a body fluid from the mammal, and (b) measuring in the profile of step a) the amount of at least one carbohydrate or a fragment derived thereof or a labeled derivative of the carbohydrate or the fragment, or a feature of at least one carbohydrate or fragment derived thereof present in the carbohydrate profile wherein at least one carbohydrate is selected from the group consisting of:

(i) GlcNAc(β-1,2)Man(α-1,3)[GlcNAc(β-1,2)Man(α-1,6)]Man(β-1,4) GlcNAc(β-1,4)[Fuc(α-1,6)]GlcNAc (glycan 1), (ii) GlcNAc(β-1,2)Man(α-1,3)[GlcNAc(β-1,4)] [GlcNAc (β-1,2)Man (α-1,6)]Man(β-1,4)GlcNAc(β-1,4)[Fuc(α-1,6)] GlcNAc (glycan 2), (iii) Gal(β-1,4)GlcNAc(β-1,2)Man(α-1,3)[GlcNAc(β-1,4)] [Gal(β-1,4) GlcNAc(β-1,2)Man(α-1,6)]Man(β-1,4) GlcNAc(β-1,4)[Fuc(α-1,6)]GlcNAc (glycan 7), (iv) Gal(β-1,4)GlcNAc(β-1,2)[Gal(β-1,4)GlcNAc(β-1,4)]Man(α-1,3)[Gal (β-1,4)GlcNAc(β-1,2)Man(α-1,6)]Man (β-1,4)GlcNAc(β-1,4)GlcNAc (glycan 8), (v) a fragment derived of glycan 1, 2, 7 or 8, (vi) a sialylated derivative of glycan 1, 2, 7 or 8, (vii) a feature of glycan 1, 2, 7 or 8 or derivative or fragment thereof. and (c) comparing the measured data obtained in step b) with measured data obtained from profiles derived from mammals free of liver fibrosis in order to detect liver fibrosis or, comparing the data obtained in step b) with previously measured data in the mammal in order to detect a change in the gradation of liver fibrosis and (d) attributing the results of the comparison obtained in step c) to detect liver fibrosis or a change in the gradation of liver fibrosis in a mammal.

Figure 5:
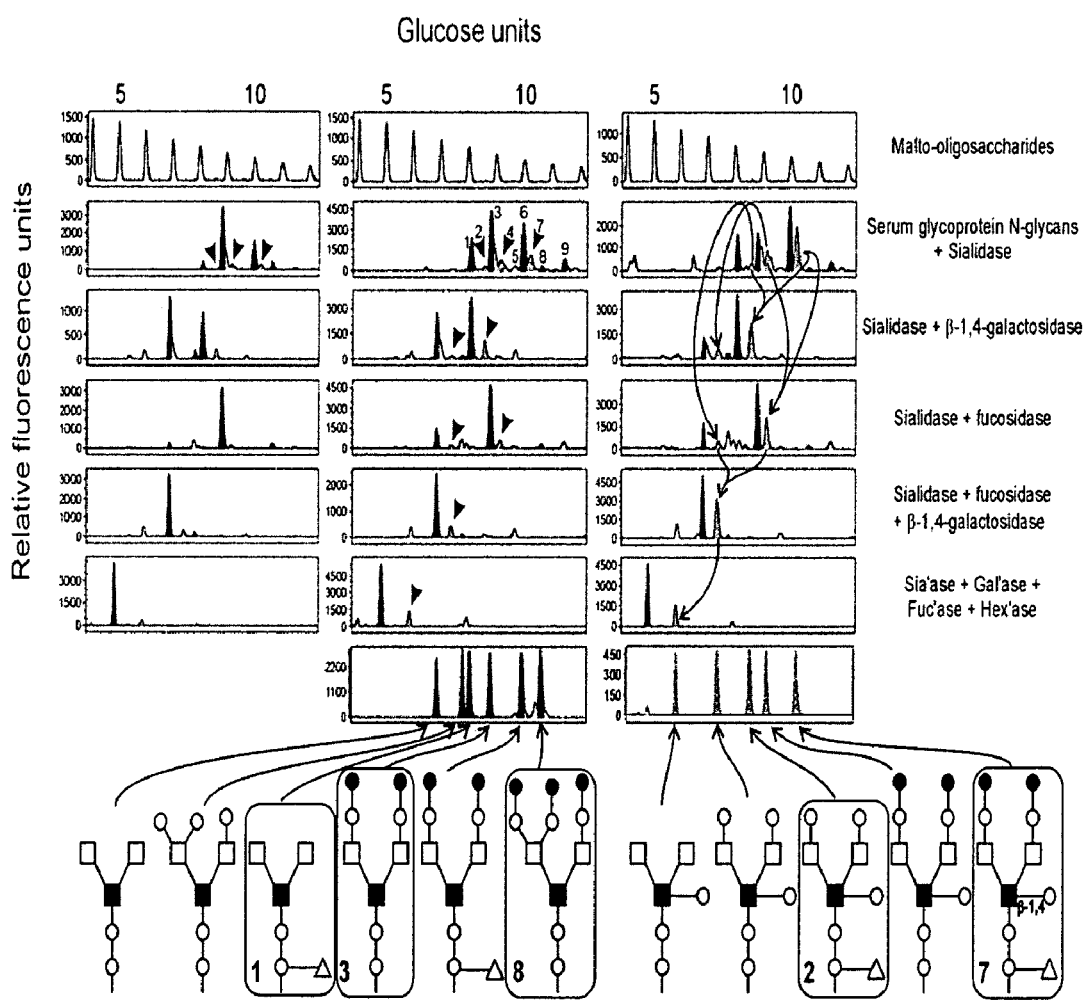
FIG. 5: Partial structural analysis of the differentially regulated N-glycans. The three columns in this figure represent the results of exoglycosidase array sequencing on the N-glycans derived from the glycoproteins in three serum samples. These samples were chosen to reflect the quantitative range of the observed alterations in this study. The leftmost sequencing column was obtained from analysis of a sample with chronic hepatitis and is representative for the control's profiles. The middle column represents a relatively mild alteration, already trespassing the cut-off values for all three cirrhosis-diagnostic variables described in the text. The right column results from analysis of one of the most affected samples. It is very useful to compare the peaks described in Example 9 over these three columns, and the possibility for this comparison greatly simplifies the peak tracking throughout the exoglycosidase sequencing panels. The peaks depicted in black do not carry a bisecting GlcNAc residue. In this respect, they can all be regarded as derivatives of the trimannosyl-GlcNAc$_2$ core oligosaccharide. The peaks depicted in grey are all modified with a bisecting GlcNAc residue and thus can all be considered as derivatives of the bisecting GlcNAc-substituted trimannosyl-GlcNAc$_2$ core oligosaccharide. The reference panels under the sequencing columns in the middle and to the right were assembled from different electropherograms, each resulting from a specific exoglycosidase digestion on reference glycans with known structure. The reference glycans used were: 1) trisialo, trigalacto triantennary; 2) bisialo, bigalacto biantennary with core-α-1,6-linked fucose (Reference panel under middle column) and 3) asialo, bigalacto biantennary with core-α-1,6-linked fucose and bisecting GlcNAc (Reference panel under rightmost column).

For the sake of clarity the structures of the peaks 1, 2, 7 and 8 correspond with the carbohydrate profile depicted in FIG. 1 and with the graphic representation of these structures in FIG. 5. The carbohydrate profile is a desialylated profile (without sialic acid on the glycans), meaning that the structures of peaks 1, 2, 7 and 8 are strictly spoken carbohydrate fragments (missing the sialic acid structures). The carbohydrates are herein presented with the IUPAC rules for nomenclature (www.chem.qmul.ac.uk/iupac/2carb/38.html), the peaks according to FIG. 1 have been identified in the present invention and are represented by their condensed and extended nomenclature. In the claims the condensed nomenclature is used. The name of the four structures is summarized here below.

Desialylated glycan structure of peak 1 from FIG. 1:
Condensed nomenclature: GlcNAc(β-1,2)Man(α-1,3) [GlcNAc(β-1,2)Man(α-1,6)] Man(β-1,4)GlcNAc(β-1,4)[Fuc(α-1,6)]GlcNAc
Extended nomenclature: β-D-GlcpNAc-(1→2)-α-D-Manp-(1→3)-[β-D-GlcpNAc-(1→2)-α-D-Manp-(1→6)]-β-D-Manp-(1→4)-β-D-GlcpNAc-(1→4)-[α-L-Fucp-(1→6)]-D-GlcpNAc Desialylated glycan structure of peak 2 from FIG. 1:
Condensed nomenclature: GlcNAc(β-1,2)Man(α-1,3) [GlcNAc(β-1,4)] [GlcNAc (β-1,2)Man(α-1,6)]Man(β-1,4)GlcNAc(β-1,4)[Fuc(α-1,6)]GlcNAc
Extended nomenclature: β-D-GlcpNAc-(1→2)-α-D-Manp-(1→3)-[β-D-GlcpNAc-(1→4)] [β-D-GlcpNAc-(1→2)-α-D-Manp-(1→6)]-β-D-Manp-(1→4)-β-D-GlcpNAc-(1→4)-[β-L-Fucp-(1→6)]-D-GlcpNAc Desialylated glycan structure of peak 7 from FIG. 1:
Condensed nomenclature: Gal(β-1,4)GlcNAc(β-1,2)Man (α-1,3)[GlcNAc(β-1,4)] [Gal(β-1,4)GlcNAc(β-1,2) Man(α-1,6)]Man(β-1,4)GlcNAc(β-1,4)[Fuc (α-1,6)] GlcNAc
Extended nomenclature: β-D-Galp-(1→4)-β-D-GlcpNAc-(1→2)-α-D-Manp-(1→3)-[β-D-GlcpNAc-(1→4)] [β-D-Galp-(1→4)-β-D-GlcpNAc-(1→2)-α-D-Manp-(1→6)]-β-D-Manp-(1→4)-β-D-GlcpNAc-(1→4)-[α-L-Fucp-(1→6)]-D-GlcpNAc Desialylated glycan structure of peak 8 from FIG. 1:
Condensed nomenclature: Gal(β-1,4)GlcNAc(β-1,2)[Gal (β-1,4)GlcNAc(β-1,4)] Man(α-1,3)[Gal(β-1,4) GlcNAc(β-1,2)Man(α-1,6)]Man(β-1,4)GlcNAc (β-1,4)GlcNAc
Extended nomenclature: β-D-Galp-(1→4)-β-D-GlcpNAc-(1→2)-[β-D-Galp-(1→4)-β-D-GlcpNAc-(1→4)]-α-D-Manp-(1→3)-[β-D-Galp-(1→4)-β-D-GlcpNAc-(1→2)-α-D-Manp-(1→6)]-β-D-Manp-(1→4)-β-D-GlcpNAc-(1→4)-D-GlcpNAc In another embodiment, the invention provides a method to detect liver fibrosis or a change in the gradation of liver fibrosis comprising the steps of (a) generating a profile of carbohydrates or fragments derived thereof, or labeled derivatives of the carbohydrates or the carbohydrate fragments, or features of the carbohydrates or the carbohydrate fragments that are determined by the structure of the carbohydrates or the carbohydrate fragments; the carbohydrates or the fragments being present on a mixture of glycoconjugates or obtained from a mixture of glycoconjugates that are present in or are derived from a sample of a body fluid from the mammal and (b) measuring the relative amount between the glycan structure 1 or a fragment thereof and the glycan structure 8 or a fragment thereof and/or the glycan structure 2 or a fragment thereof and the glycan structure 8 or a fragment thereof and/or the glycan structure 7 or a fragment thereof and the glycan structure 8 or a fragment thereof or a fragment, sialylated derivative or feature thereof and c) comparing the measured data obtained in step b) with measured data obtained from profiles derived from mammals free of liver fibrosis in order to detect liver fibrosis or, comparing the data obtained in step b) with previously measured data in the mammal in order to detect a change in the gradation of liver fibrosis and (d) attributing the results of the comparison obtained in step c) to detect liver fibrosis or a change in the gradation of liver fibrosis in a mammal.

In another embodiment, the invention also includes a diagnostic kit for performing diagnosis of liver fibrosis or for detecting a change in the gradation of liver fibrosis. For example, a diagnostic kit can be made for performing fluorophore assisted carbohydrate electrophoresis diagnosis of liver fibrosis. As another example, a diagnostic kit can be made for performing mass spectrometric diagnosis of liver fibrosis. Fluorophore assisted carbohydrate electrophoresis diagnosis kits provide collections of reagents required for performing the diagnosis of liver fibrosis. Suitable kits enable laboratories to conveniently perform fluorophore assisted carbohydrate electrophoresis diagnosis. Kits may include reagents for performing tests to identify liver fibrosis. Kits may include diagnostic standards, fluorescent label, blotting and binding materials, e.g., membranes, carbohydrate specific binding reagents, lectins, instructions, sample containers, and polyacrylamide gel reagents, precast gels, enzyme buffers, reducing agents (for use in the fluorophore labeling of carbohydrates), and glycosidase enzymes (e.g., sialidase, galactosidase, fucosidase) capable of catalyzing reactions that structurally alter diagnostic carbohydrates. More complete kits may include equipment for performing fluorophore assisted carbohydrate electrophoresis, such as polyacrylamide gel apparatus, CCDs, laser, DNA sequencer, computers, software, and the like. Reagents included in fluorophore assisted carbohydrate electrophoresis diagnosis kits are preferably provided in pre-measured amounts. The kits preferably include the instructions for carrying out the fluorophore assisted carbohydrate electrophoresis method of the present invention.

The diagnostic test is useful in practice because it is sufficiently easy to apply on a large scale by normally trained laboratory staff. Furthermore, since electrophoresis-based high-resolution and high-sensitivity analyzers for DNA sequencing and mutation detection are already present in a rapidly increasing number of clinical laboratories or are affordable for most clinical laboratories, the novel diagnostic glycomics test for liver fibrosis can be run on them. Moreover, the available range of DNA-analyzers allows for the sample throughput to be easily scaled from just a few to hundreds of samples per day per machine, depending on the demand of each laboratory. This DNA-analysis equipment offers the added advantage of automation, reducing the complexity of the overall analytical process. The profiling on the total mixture of glycoproteins increases the tolerance of the test for small inter-individual variations of the abundance and the glycosylation pattern of each individual glycoprotein in the mixture and thus allows more robust testing than the current classical approaches where the glycosylation is studied on purified glycoproteins.

In another embodiment, the method for the detection of liver fibrosis further comprises clinical chemistry parameters and/or histological data. Thus, the present invention can also be conveniently carried out in combination with clinical chemistry parameters and/or histology and/or imaging parameters. Measurement of clinical chemistry parameters comprises measurement of levels of bilirubin and/or albumin and/or prothrombin time and/or C-reactive protein and/or IgA abundance and/or serum hyaluronic acid concentration and/or aminotransferases and/or several liver metabolism test known in the art. In a specific embodiment, the fibrotest binary logistic regression model as described in the incorporated WO 0216949 is calculated and is used in combination with the diagnostic test of the present invention.

Histology comprises liver biopsies. Imaging comprises ultrasound and/or CT-scan and/or MRI-scan and/or imaging of radioactive tracers specific for the liver.

The examples which follow are offered as descriptive of certain embodiments. As such they are exemplary only and are not limiting in their nature.

EXAMPLES

1. Data Collection and Processing

Figure 2:
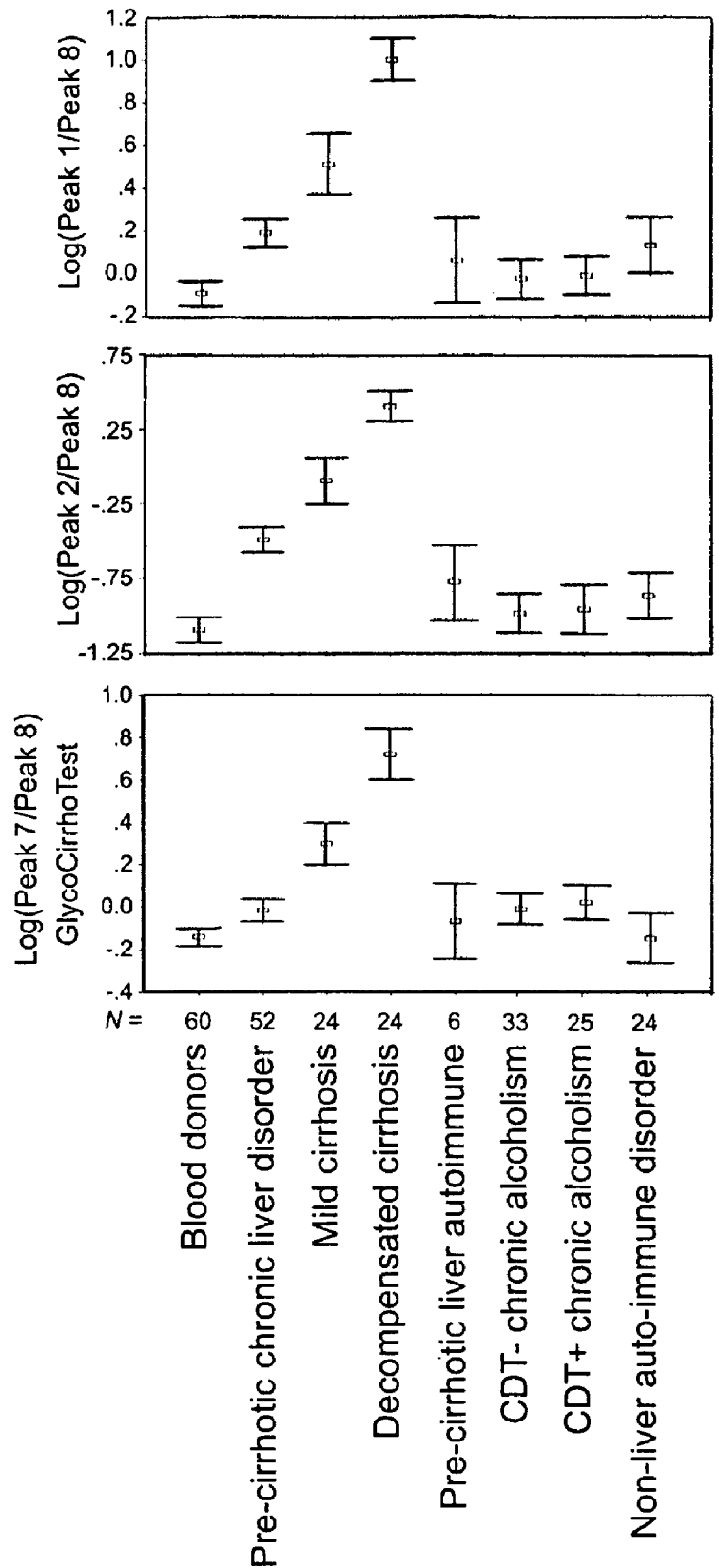
FIG. 2: Trends in the derived diagnostic variables. The serum samples were classified in nine clinically relevant groups. Three diagnostic variables were derived from profiles as shown in FIG. 1: Log(Peak 1/Peak 8), Log(Peak 2/Peak 8) and Log (Peak 7/Peak 8). The latter was renamed as GlycoCirrhoTest because of its high diagnostic efficiency for cirrhosis. Note that the ordinate scale is logarithmic. All three variables show a clear trend towards higher average values with increasing severity of the liver disease, and especially so in cirrhosis (error bars are 95% confidence intervals for the mean).
Figure 6:
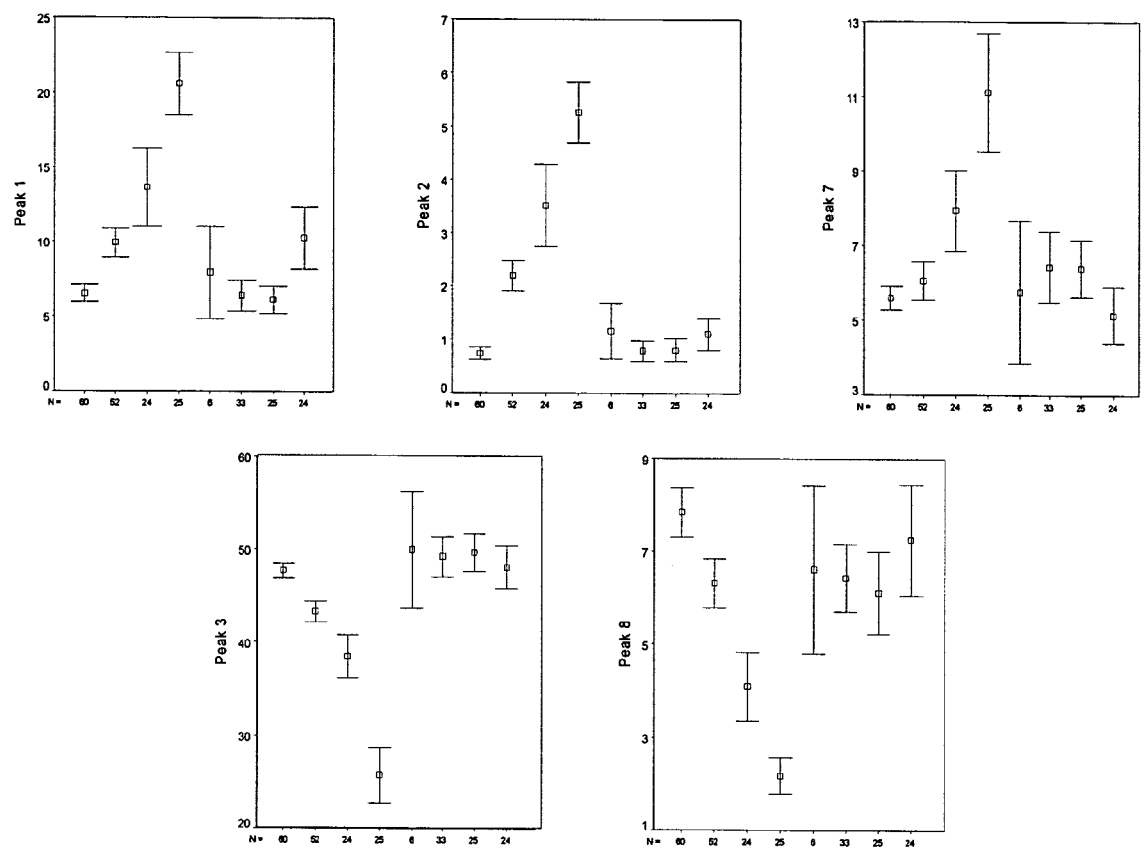
FIG. 6: Data distortion for the five peaks in the serum N-glycome profiles that show the desired trend: progressively increased or decreased values with increasing liver disease severity. The grouping is the same as in FIG. 1. These peaks were further used to develop the diagnostic variables described in the text.

A desialylated N-glycan profile (FIG. 1) was obtained for the 248 serum samples of the subjects under study (see, serum samples and clinical diagnosis, Table 1), and we quantified 14 peaks that were detectable in all samples. Their abundance was normalized to the total peak height intensity of these 14 peaks. Mild cirrhosis is defined here as cases having within-reference range values for the three biochemical components of the classical Child-Pugh cirrhosis classifier (serum albumin, total bilirubin and International Normalized Ratio, the latter is a measure for clotting speed). We define cirrhosis cases with out of-reference range values for one or more of these three markers as "decompensated." Thus, the group of "mild cirrhosis" cases is those who would be misclassified as "non-cirrhotic" by the current biochemical cirrhosis assessment, and it is obviously for this subgroup that novel biomarkers mean a real improvement. We found that five of the 14 peaks in the serum N-glycome showed the desired trend of having a progressively higher or lower abundance in the order: healthy blood donors </> non-cirrhotic chronic liver disorder < > mild cirrhosis </> decompensated cirrhosis, while having a relatively "normal" abundance for the control groups (FIG. 6). These increases in abundance of Peaks 1, 2 and 7 are inversely correlated with the decreases in abundance of Peaks 3 and 8 (Pearson's r varies from −0.5 to −0.8, for all: P<0.0001). Therefore, we created three new variables (FIG. 2) by scaling the increased-abundance Peaks 1, 2 and 7 to the decreased-abundance Peak 8 and subsequently log-transformed these new variables to normalize the distributions. In this way, we have summarized the trends of interest in the data in three variables, necessitating the quantification of only four of the peaks in the serum N-glycome profile (these are boxed in FIG. 1; taking also peak 3 into account did not add extra diagnostic information following an assessment as described below).

2. Cirrhosis Detection

Figure 3:
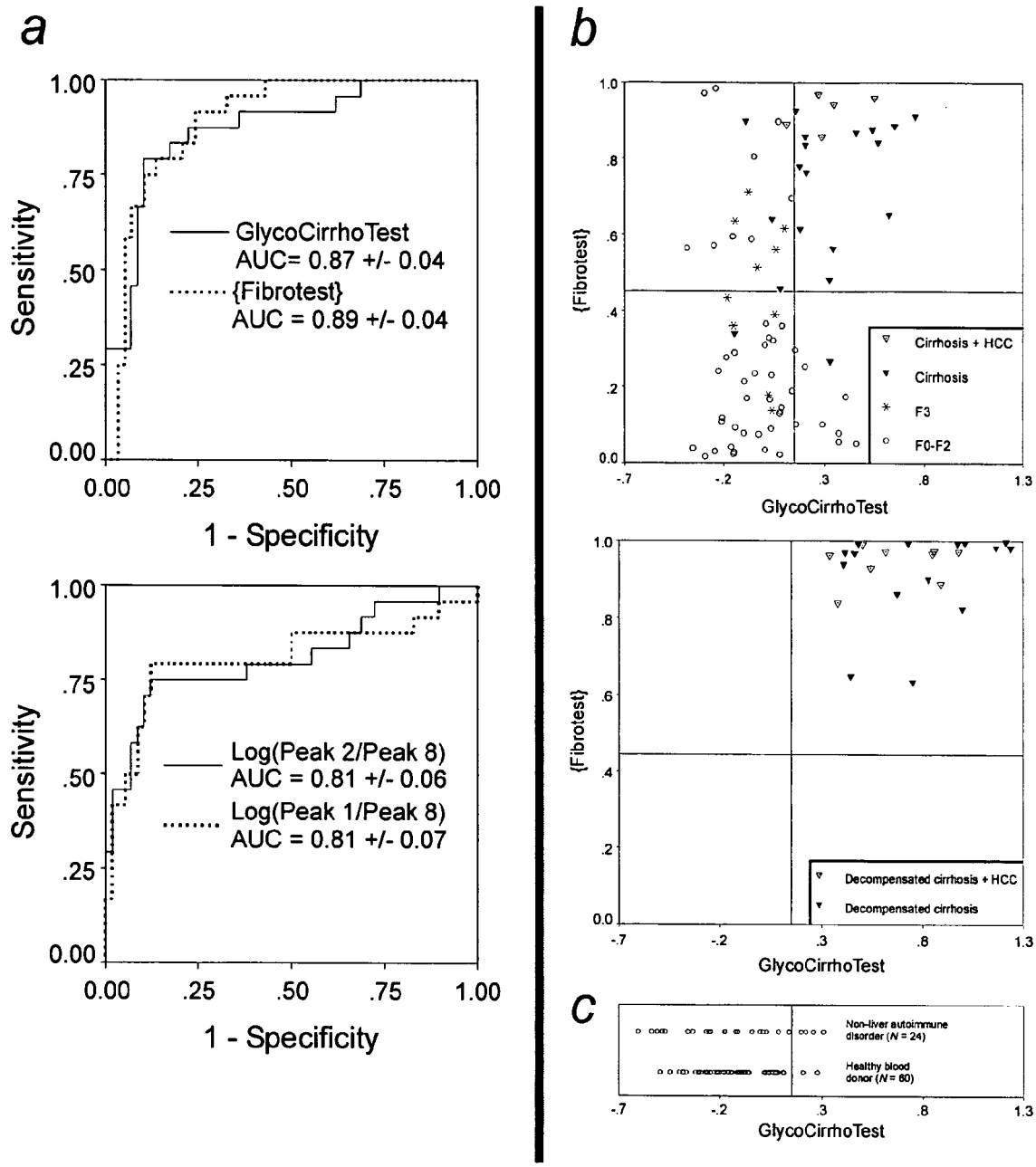
FIG. 3: Classification efficiency of the three derived variables using ROC analysis. a) ROC curve analysis was performed to evaluate the efficiency of the three variables shown in FIG. 2 in differentiating the sample group with mild cirrhosis and the group with pre-cirrhotic chronic liver disease. The cut-off values determined from the GlycoCirrhoTest and from the {Fibrotest} ROC curves were used in section b of this figure to divide the two-dimensional scatterplot fields in quadrants. b) Two-dimensional scatterplots classifying the cirrhosis sample group and the pre-cirrhotic chronic liver disease group. Top panel: biochemically compensated cirrhosis cases with/without HCC are detected with 75% sensitivity and 100% specificity. Middle panel: biochemically decompensated cirrhosis cases with/without HCC are detected with 100% sensitivity. c) Test of GlycoCirrhoTest cutoff for a general population sample (Red Cross blood donors) and of patients with non-liver auto-immune disease. See text for explanation. These individuals are normally not candidates for biopsy, but were studied to learn about possible interference of changes in IgG glycosylation, typical for certain auto-immune diseases.

For one of the three new variables [Log(Peak 7/Peak 8); herein renamed GlycoCirrhoTest], the mean of the mild cirrhosis group (including those mild cirrhosis cases complicated by hepatocellular carcinoma) was significantly different from the mean of all other sample groups at the 0.005 significance level (ANOVA, Tukey's HSD). The means of the other two serum glycome-derived variables were also significantly different from the mean of all other sample groups, but at a lower significance level ($\alpha_{FW}$=0.05). The ability of the three glyco-parameters and of the {Fibrotest} to discriminate between patients with mild cirrhosis (as defined above) and those with pre-cirrhotic chronic liver disease was evaluated with non-parametric Receiver Operating Characteristic (ROC) curve analysis.[16,17] The results of the ROC analysis indicate classification efficiencies as measured by the Area Under the Curve (AUC) of 85-90% for both GlycoCirrhoTest and {Fibrotest} (FIG. 3a, top). The other two serum-glycome derived parameters had a somewhat lower classification efficiency (AUC=0.81±0.07 for Log(Peak 1/Peak 8) and AUC=0.81±0.06 for Log(Peak 2/Peak 8; FIG. 3a, bottom). We then calculated the cut-off values from the ROC curves and used these cut-off values to classify the patients via two-dimensional scatter plots (FIG. 3b, top panel). The combination of the two most performant biomarkers for cirrhosis detection in this study (the glycomics-based GlycoCirrhoTest and the {Fibrotest} binary logistic regression model) yields 100% specificity for the detection of mild cirrhosis, with a sensitivity of 75% (18/24). The overall classification efficiency was 93% (76/82). The group of those chronic liver disorder patients with a decompensation in at least one of the classical biochemical markers for cirrhosis (albumin, bilirubin, INR) was also classified using the above-calculated cut-off values (FIG. 3b, middle panel), which revealed 100% sensitivity for this advanced cirrhosis.

So, in the group of patients that were liver biopsy candidates due to a diagnosed chronic liver disorder, there were no false positives on our novel marker combination for cirrhosis detection, and biochemically compensated cirrhosis cases were detected with 75% sensitivity, whereas this was 100% for biochemically decompensated cases.

3. Behavior of the Diagnostic Variables in Pre-Cirrhotic Fibrosis Stages

Figure 4:
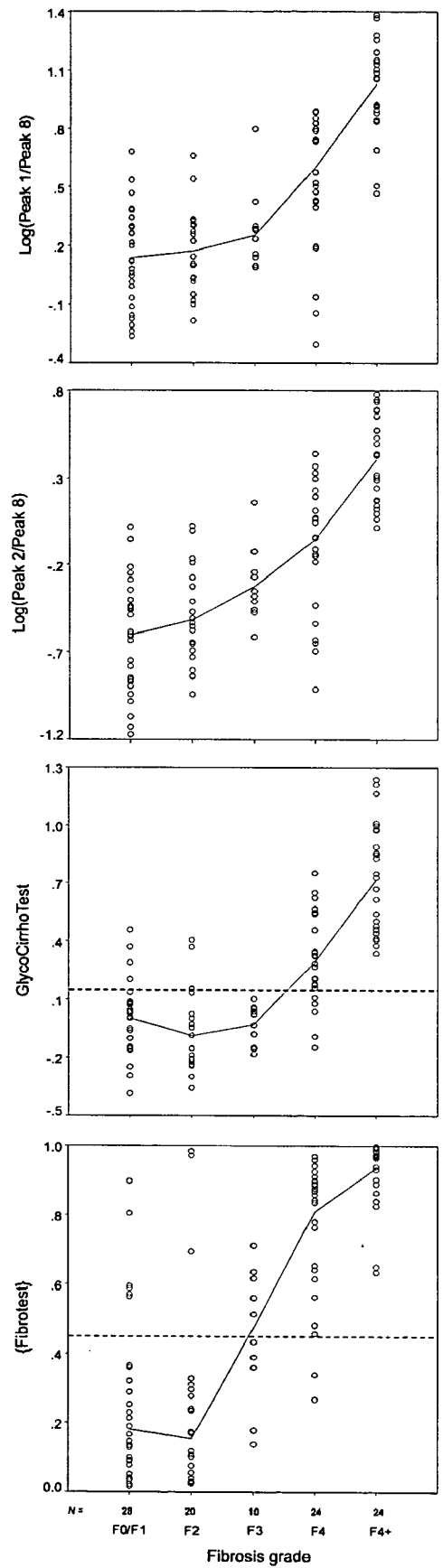
FIG. 4: Values of some of the glycome markers gradually increase with the fibrosis stage. The data for the three glycome-derived markers were plotted against the fibrosis stage. Cases with stage F0 and F1 (no or portal fibrosis) were grouped, as there were only four F0 cases, and as this grouping is clinically significant in that normally no anti-HCV treatment is initiated for these patients. Stage F4+ indicates biochemically decompensated cirrhosis. Trendlines were generated by the non-parametric Lowess regression. The horizontal lines in the lower two panels represent the ROC-determined cut-off values for cirrhosis detection. Note the relative stability of GlycoCirrhoTest from F0/F1 up to F3, only increasing from F4. Also note the expected sigmoidal behavior of the {Fibrotest} model. Interestingly, both Log(Peak 1/Peak 2) and especially Log(Peak 2/Peak 8) gradually increase with the fibrosis stage. For Log(Peak 2/Peak 8), linear Spearman Rank correlation yields a high correlation coefficient of 0.76.

The superior classification efficiency of GlycoCirrhoTest over the other two serum-glycome derived biomarkers is explained by the trends in the data, when plotted according to the histologically determined liver fibrosis stage[18] (FIG. 4). Whereas Log(Peak 1/Peak 8) and especially Log(Peak 2/Peak 8) raise gradually with increasing fibrosis stage, from F0/F1 onwards, GlycoCirrhoTest stays stable or even goes down a little from F0/F1 up to F3, and only goes up in cirrhosis. It is remarkable that the correlation between the fibrosis stage and the values for Log(Peak 2/Peak 8) approaches linearity (p=0.76 by Spearman Rank Correlation), which makes it a very promising marker for the follow-up of fibrosis progression (or lack thereof). As for the {Fibrotest} model, a sigmoidal increase of its values with increasing fibrosis stage is observed, as expected (binary logistic regression models regress on a 0-1 interval, with ensuing asymptotic behavior at both extremes). In previous studies,[14] the transition in the sigmoidal curve was reported to lay at about F2. In our study, we find that the transition lays at F3. It is unclear what the reason for this difference might be.

4. Assessment of GlycoCirrhoTest in Other Diseases and in a General Population Sample To gain a broader understanding of the characteristics of the novel GlycoCirrhoTest, we classified a control group of Red Cross blood donors (general population sample, HBV, HCV and HIV negative) with the cut-off value that was optimized for cirrhosis detection. Only two cases (on 60; 3%) scored mildly positive (FIG. 3b, lower panel). Regular alcohol consumption is no exclusion criterion for blood donation (and alcohol abuse can go unnoticed in this setting), and this is the main cause of cirrhosis in low HCV-incidence regions such as Flanders, Belgium, where the study was performed. Combined with the rather high median age of this group (61 y), a rate of 2-3% compensated cirrhosis is within the line of expectation.[19] We included a control group consisting of 24 patients with auto-immune diseases, because undergalactosylation of serum IgG has been well documented in most of these diseases, especially in rheumatoid arthritis.[20] It is obvious that IgG glycan modifications could be reflected in the glycan pattern of total serum glycoproteins, as IgG is present at about 11 g/l in serum and is the major non-liver produced glycoprotein in this fluid. Thus, we micropurified the immunoglobulins from the serum of these 24 patients and of six members of our healthy blood donor group using protein L affinity chromatography, and an N-glycan profile of these purified immunoglobulin preparations was obtained. As expected, a relatively strong undergalactosylation was detected in the auto-immune group, mainly reflected in an increased abundance of the non-galactosylated core-α-1,6-fucosylated glycan (structure 1 in FIG. 1, average 55% higher than in the controls, P=0.01). Moreover, we found a strong increase in the level of substitution of the immunoglobulin N-glycans with a bisecting GlcNAc residue, reflected in a doubling on average of the abundance of the glycan with structure 7 of FIG. 1 (P<0.0001). However, these increases were in most cases insufficient to disturb the N-glycan pattern of total serum glycoproteins so much that they would score positive on GlycoCirrhoTest (4/24 positive). We could not assess Fibrotest in these patients due to insufficient available serum. To assess whether the presence of increased levels of serum Carbohydrate Deficient Transferrin[21] (CDT) influenced the serum N-glycome cirrhosis-diagnostic parameters, we obtained serum samples from chronic alcoholism patients with and without such an elevated CDT. The means for the three cirrhosis-diagnostic parameters described above in the CDT positive group were not significantly different from the means in the group with normal levels of CDT (P>0.1, Student's t-test) which shows that differences in CDT levels do not influence our cirrhosis markers.

5. Partial Structural Analysis of the Differentially Abundant N-glycans

We could obtain significant structural information on the differentially regulated serum N-glycans in liver cirrhosis, helped by the information in a literature report that describes a three-dimensional HPLC mapping of the N-glycans present on the glycoproteins in "healthy" human serum.[22] Moreover, from our diagnostic studies, samples were available with a broad quantitative range in the peaks of interest. This was very helpful in "tracing" the peaks of interest through post-exoglycosidase-array profiles. The exoglycosidase sequencing of three of these samples is shown in FIG. 5. A full description of the structural analysis can be found in Example 9. The summarized conclusions from this structural analysis are that there is an increased abundance of undergalactosylated N-glycans (Peaks 1 and 2) in liver cirrhosis, an increase of N-glycans modified with a bisecting N-acetylglucosamine (GlcNAc) residue (Peaks 2 and 7) and a decrease of fully galactosylated bi-and triantennary N-glycans (Peaks 3 and 8).

6. Technology Development for Implementation in Routine Molecular Diagnostics Laboratories.

Figure 7:
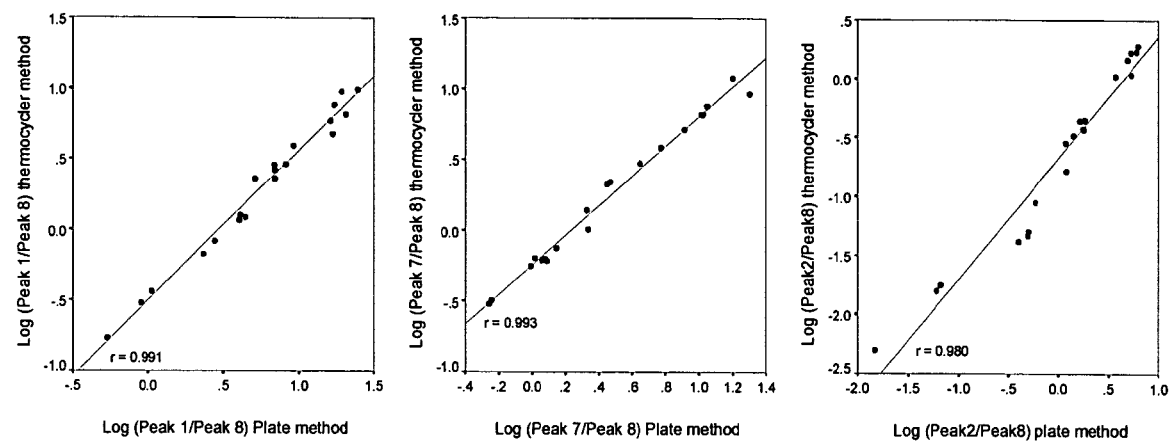
FIG. 7: Strict linear correlation between the cirrhosis-detecting parameters measured by the Inmobilon-P plate based sample preparation method and the new thermocycler based method. Twenty randomly chosen serum samples from the chronic liver disease group and from the healthy control group were analyzed using both sample preparation methods. The three diagnostic parameters Log (Peak 1/Peak 8), Log (Peak 2/Peak 8) and Log (Peak 7/Peak 8) show an almost perfect linear correlation between the two methods (Pearson's r≧0.98). This shows that the validity of the diagnostic results is conserved regardless of the sample preparation method.

6.1 Sample Preparation Using only a PCR Thermocycler:

Having obtained the above evidence that serum N-glycome profiling has diagnostic utility, we introduced further simplifications in our sample preparation protocol. Using a standard heated-lid PCR thermocycler a procedure was developed that only involves fluid addition/removal and dilution to produce ready-to-analyze labeled N-glycans from serum in less than eight hours, with little hands-on time (see, Methods section). The basis of the resulting protocol is that the serum glycoprotein concentration is very high and that our glycan analytical method is very sensitive (15 fmol easily detectable). Consequently, there is a broad margin between the amount of available N-glycans in a small serum sample and the amount that is needed analytically. This broad margin can be sacrificed to making some steps in the sample preparation protocol less efficient, but easier to apply. This protocol was tested on 20 of the serum samples that had been analyzed before with our standard sample preparation method. The values for the three previously described diagnostic variables determined by both techniques were very strongly linearly correlated (Pearson's $r>0.98$; FIG. 7), demonstrating that the novel thermocycler-based method can substitute for the more laborious Immobilon-P-plate based sample preparation procedure that we used before. In our current laboratory practice, we have assembled all the reagents for this protocol in a kit form that allows the parallel preparation of 48 or 96 samples.

Figure 8:
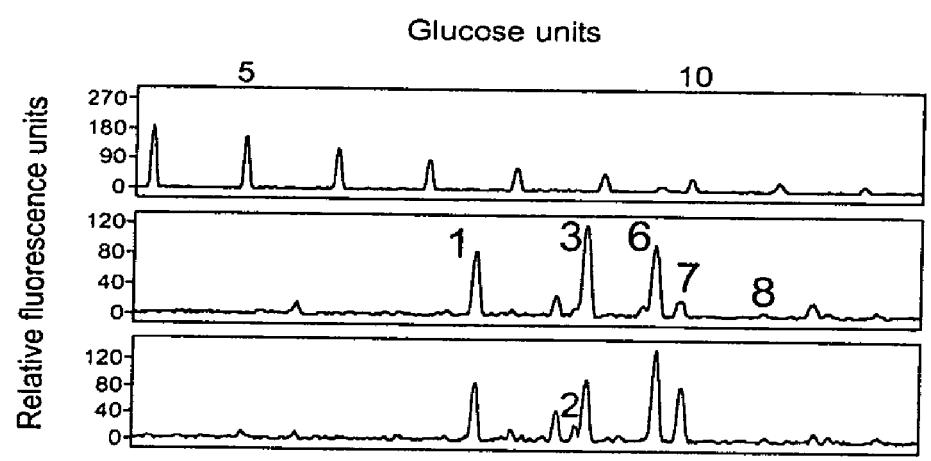
FIG. 8: Total serum protein N-glycan profile analysis on ABI310. The two cirrhosis samples of FIG. 5 were re-analyzed using the capillary electrophoresis-based ABI310 DNA-analyzer. As can be noted from a comparison of the dextran hydrolysate electropherogram in this figure and in FIG. 5, the analysis on ABI310 has a significantly better resolution than on ABI377 gels. The relative migration behavior of the N-glycans is somewhat different between both methods, presumably because the capillary method uses a linear polyacrylamide as the separation matrix instead of a cross-linked polyacrylamide gel.

6.2 Capillary Gel Electrophoresis Profiling of the Serum N-glycome Using the ABI 310 DNA-analyzer Capillary gel electrophoresis-based DNA analyzers are in widespread use in molecular pathology laboratories, where they are used for diagnostic assays involving DNA sequencing or high-resolution DNA fragment analysis (solid tumor analysis, infectious disease diagnosis, . . . ). These analyzers are rapidly replacing the older gel-based DNA analyzers due to their level of automation and ease of use, which makes them more suitable for operation in clinical diagnostic laboratories. Therefore, to complete the implementation of our glycomics assay on the standard equipment of molecular pathology laboratories, we optimized the analysis of the desialylated total serum N-glycome on the ABI 310 single capillary DNA analyzer. Only little modification was required to standard DNA analysis procedures to obtain robust profiling in 18 minutes, with even higher resolution than obtained on the gel-based ABI 377 (FIG. 8). This allows the unattended analysis of 48 APTS-labeled serum glycan samples in an overnight run. In combination with the thermocycler-based sample preparation, we thus achieved a 24 hour turnaround time for 48 samples with no more manual intervention than is needed for the typical DNA fragment analysis reaction in a molecular pathology laboratory. The throughput could easily be increased if necessary, as multi-capillary sequencers are available.

7. Serum Samples and Clinical Diagnosis

The study group of patients with chronic liver disorders consists of liver-biopsy candidate patients referred to the Department of Gastroenterology and Hepatology at the University Hospital Ghent, regardless of underlying etiology (viral, alcoholic, auto-immune, cryptogenic, see below). The following data were obtained: patient's age and sex, serum albumin, total bilirubin, INR, AST, ALT, GGT, total serum protein, $\alpha_2$-macroglobulin, haptoglobin and apolipoprotein A1. Serum albumin, total bilirubin, AST, ALT, GGT and total serum protein were measured on the Modular analyzer (Roch Diagnostics, Basel, Switzerland). Haptoglobin, $\alpha_2$-macroglobulin and apolipoprotein A1 were measured by fixed-time immunonephelometry on a BN II analyzer (Dade Behring, Marburg, Germany). The $\alpha_2$-macroglobulin and haptoglobin assays were calibrated against the international CRM 470 reference material (Dati, F. et al. (1996) *Eur. J. Clin. Chem. Clin. Biochem.* 34, 517-520). Apolipoprotein A1 was standardized according to the IFCC standard (Albers, J. J. & Marcovina, S. M. (1989) *Clin. Chem.* 35, 1357-1361). Patients for whom one or more of the above-mentioned data points were missing were excluded from the study. On the basis of $\alpha_2$-macroglobulin, haptoglobin, GGT, age, bilirubin, apolipoprotein A1 and sex, a score was calculated for the {Fibrotest} binary logistic regression model.

This binary logistic regression model known as Fibrotest was developed by Dr. T. Poynard (ref. 14, 15 and WO0216949) We have used the following formula (derived from WO0216949) in the present invention: $f=4.467 \times \text{Log}[\alpha 2\text{-macroglobulin (g/l)}] - 1.357 \times \text{Log [Haptoglobin (g/l)]} + 1.017 \times \text{Log [GGT (IU/l)} + 0.0281 \times \text{Age (in years)]} + 1.737 \times \text{Log [Bilirubin (}\mu\text{mol/l]} - 1.184 \times [\text{ApoA1 (g/l)}] + 0.301 \times \text{Sex (female=0, male=1)} - 5.540$. We here refer to the binary logistic regression model as applied in WO0216949. The patients with decompensated cirrhosis on biochemical grounds according to the Child-Pugh classification (at least one of the following: serum albumin <3.5 g/dl; serum total bilirubin>2 mg/dl, International Normalized Ratio>1.7) were classified in the "Decompensated cirrhosis" group (N=24) and no biopsy was performed to avoid unnecessary study-associated risk to these participants. In the 82 other patients (where contra-indications for a liver biopsy were absent), the stage of liver fibrosis was assessed by a percutaneous liver biopsy, scored according to the METAVIR criteria by a pathologist blinded to the GlycoCirrhoTest and {Fibrotest} results. Patients who refused to undergo a biopsy, or for whom an interpretable biopsy was not available were excluded from the study. All collected data and the etiology of the chronic liver disease of the 106 patients described above can be found in Table 1.

TABLE 1

Data are the median (interquartile range) or number of cases (N %).
Characteristics of the 106 chronic liver disease patients under study.

| Characteristics | Study group (N = 82) | Cirrhosis with biochemical decompensation (N = 24) |
|---|---|---|
| Age, years | 42 (35-60) | 58 (52-62) |
| Male gender | 45 (55%) | 19 (79%) |
| Etiology | | |
| Chronic alcoholism | 4 (5%) | 12 (50%) |
| HCV | 63 (77%) | 8 (33%) |
| HBV | 6 (7%) | 2 (8%) |
| Auto-immune | 7 (9%) | 1 (4%) |
| Cryptogenic | 2 (2%) | 1 (4%) |
| Fibrosis stage | | |
| No fibrosis (F0) | 4 (5%) | / |
| Portal fibrosis (F1) | 24 (29%) | / |
| Few septa (F2) | 20 (24%) | / |
| Numerous septa (F3) | 10 (12%) | / |
| Cirrhosis (F4) | 19 (23%) | 15 (62%) |
| F4 + HCC | 5 (7%) | 9 (38%) |
| Biochemical markers | | |
| INR | 1.07 (1.00-1.18) | 1.4 (1.24-1.54) |

TABLE 1-continued

Data are the median (interquartile range) or number of cases (N %).
Characteristics of the 106 chronic liver disease patients under study.

| Characteristics | Study group (N = 82) | Cirrhosis with biochemical decompensation (N = 24) |
|---|---|---|
| Albumin (g/dl) | 4.2 (3.9-4.6) | 2.7 (2.5-3.2) |
| Total bilirubin (µmol/l) | 9 (5-14) | 55 (24-92) |
| Total serum protein (g/dl) | 7.5 (7.0-8.0) | 6.7 (6.3-7.1) |
| ALT (IU/l) | 23 (14-38) | 10 (7-15) |
| AST (IU/l) | 30 (16-47) | 27 (19-62) |
| GGT (IU/l) | 45 (22-128) | 138 (47-224) |
| α2-macroglobulin (g/l) | 1.98 (1.54-2.49) | 1.77 (1.09-2.37) |
| Apolipoprotein A1 (g/l) | 1.34 (1.06-1.65) | 0.46 (0.28-0.84) |
| Haptoglobin (g/l) | 0.73 (0.36-1.06) | 0.01 (0.01-0.40) |

The diagnosis of chronic hepatitis B and C was made by a raise in ALT level (above the upper limit of normal) in at least two blood samples over a time period of six months in the presence of either detectable hepBsAg and HBV DNA or detectable anti-HCV antibodies and HCV RNA. The diagnosis of autoimmune hepatitis was made according to the criteria published by the International Autoimmune Hepatitis Group (Johnson, J. L. & McFarlane, I. G. (1993) Hepatology 18, 998-1005). A history of chronic alcohol abuse was established by clinical interview.

In the patients with cirrhosis, the diagnosis of hepatocellular carcinoma (HCC) was made by detection of a rise in α-fetoprotein and one imaging technique (CT or MRI) demonstrating a hypervascular lesion. In the absence of a rise in α-fetoprotein, HCC was diagnosed when both imaging techniques demonstrated a hypervascular region. In patients where there was doubt about the diagnosis, a Trucut needle biopsy of the focal lesion was performed. The clinical center where the diagnosis was performed is the reference center for HCC for Flanders, a low-incidence region for HCC of about six million inhabitants, mainly Caucasian.

We analyzed samples of 58 patients with suspected chronic alcohol abuse and admitted for this reason to the Department of Psychiatry, Academic Hospital Stuivenberg in Antwerp (a major city in the Flanders region). Carbohydrate Deficient Transferrin was measured by the % CDT-TIA test, Axis Biochemicals, Oslo, Norway) and the sample group was divided into two subpopulations, one being positive on the CDT test (more than 6% CDT) and the other, negative. The specifics of the psychiatric clinical setting did not obtain more detailed information on this patient group, so we could not assess the liver disease stage and only use this patient group here to study the influence of elevated levels of CDT on our cirrhosis-diagnostic markers. Twenty-four samples were included of patients with either rheumatoid arthritis, ankylosing spondylitis or Crohn's disease, diagnosed with these disorders by specialized clinicians in the Rheumatology Department of the University Hospital Ghent.

To establish reference values for the measured glycans, a control group of 60 blood donors compliant with Red Cross health standards (negative for HBV, HCV and HIV) was studied. These samples were obtained from the Transfusion Center of the Red Cross in Ghent, Belgium.

8. Purification of Serum Immunoglobulins using ProtL Affinity Chromatography, and N-glycan Profiling of the Resulting Preparations Five µl serum was mixed with 130 µl phosphate buffered saline (PBS) and incubated with 40 µl Protein L-agarose affinity resin (Pierce Biotechnology, Rockford, Ill.) for one hour on a rotating wheel. Subsequently, the resin was captured on a Durapore membrane-lined 96-well plate (Millipore, Bedford, Mass.) and washed eight times with 300 µl PBS. Then, the bound immunoglobulins were eluted twice with 250 µl 0.1 M glycine pH=2.0. The immunoglobulins in these preparations were bound to Immobilon P membrane in a 96-well plate and the rest of the N-glycan analytical procedure was as described (Callewaert, N. et al. (2001) Glycobiology 11, 275-281). The seven most prominent peaks in the profile (not shown) accounting for >95% of the total signal intensity were quantified, and normalized to the total signal intensity. The data for Peaks 1 and 7, relevant for this study, are shown below (Table 2).

TABLE 2

Quantification of relevant N-glycans on purified immunoglobulins.

| Patient identifier | Clinical diagnosis | % Peak 1 in immunoglobulin N-glycan profile | % Peak 7 in immunoglobulin N-glycan profile |
|---|---|---|---|
| CD5 | Crohn's disease | 12.80 | 15.40 |
| CD7 | Crohn's disease | 10.53 | 17.10 |
| CD9 | Crohn's disease | 26.26 | 12.01 |
| CD14 | Crohn's disease | 22.74 | 17.68 |
| CD17 | Crohn's disease | 20.05 | 15.03 |
| CD19 | Crohn's disease | 17.05 | 22.53 |
| CD22 | Crohn's disease | 14.67 | 22.15 |
| CD31 | Crohn's disease | 22.22 | 16.84 |
| AS1 | Ankylosing spondylitis | 32.31 | 13.61 |
| CS70 | Ankylosing spondylitis | 30.33 | 14.10 |
| AS2 | Ankylosing spondylitis | 31.76 | 12.06 |
| AS3 | Ankylosing spondylitis | 28.90 | 15.26 |
| CS17 | Ankylosing spondylitis | 39.56 | 12.59 |
| CS13 | Ankylosing spondylitis | 31.58 | 17.50 |
| AS4 | Ankylosing spondylitis | 17.57 | 13.16 |
| CS28 | Ankylosing spondylitis | 29.43 | 16.54 |
| RA146 | Rheumatoid arthritis | 35.66 | 9.16 |
| RA248 | Rheumatoid arthritis | 40.29 | 13.57 |
| RA212 | Rheumatoid arthritis | 16.30 | 15.59 |
| RA226 | Rheumatoid arthritis | 19.10 | 10.14 |
| 61.00 | Rheumatoid arthritis | 34.32 | 22.63 |
| RA99 | Rheumatoid arthritis | 19.98 | 21.16 |
| RA117 | Rheumatoid arthritis | 21.33 | 15.24 |
| 85.00 | Rheumatoid arthritis | 33.62 | 12.46 |
| Average +/− SD | | 25.3 +/− 8.6 | 15.6 +/− 3.7 |
| 74M | Healthy blood donor | 18.00 | 5.01 |
| 65M | Healthy blood donor | 17.36 | 10.92 |
| 67M | Healthy blood donor | 18.68 | 7.29 |
| 80M | Healthy blood donor | 17.49 | 8.02 |
| 50M2 | Healthy blood donor | 15.45 | 8.22 |
| 56M1 | Healthy blood donor | 10.89 | 7.13 |
| Average +/− SD | | 16.3 +/− 2.9 | 7.8 +/− 1.9 |

9. Partial Structural Analysis of the Differentially Regulated N-glycans (see, FIG. 5)

In a parallel study (Callewaert, N. et al. (2003) Glycobiology 13, 367-375) we already assigned the structure of four of the major peaks in the profile of healthy serum (structures and their exoglycosidase products shown as black peaks in FIG. 5). The availability of these structures considerably simplified the task of tracing the remaining, differentially regulated peaks through the profiles. The reference panels in FIG. 5 (panels at the bottom of column 2 and 3) were generated by performing digestions with different mixtures of exoglycosidases on highly purified commercially available (Glyko, Novato, Calif.) reference glycans with the desialylated structures 6, 7 and 8 (numbering of FIG. 5). In all cases, the expected digestion products were obtained. To compress the size of FIG. 5 the electropherograms of these digestions of structures 6 and 8 were combined in one panel, shown at the bottom of the second column of FIG. 5. The electropherograms of digestion reactions on structure 7 (carrying a bisecting GlcNAc residue) were combined in the panel shown at the bottom of the third column of FIG. 5. The different peaks are not discussed in numerical order, but rather in an order that should facilitate the argument.

Peak 3

The structure of Peak 3 was determined (Callewaert, N. et al. (2003) *Glycobiology* 13, 367-375) to be biantennary, bi-β-1,4-galactosylated. Down-regulation of this glycan in HCC and/or cirrhosis is consistent with the increased abundance of its undergalactosylated counterpart and with the increase of other biantennary glycans, for which this basic biantennary substrate is the precursor.

Peak 8

Peak 8 was determined to represent the 2,4-branched triantennary, tri-β-1,4-galactosylated glycan structure (Callewaert, N. et al. (2003) *Glycobiology* 13, 367-375).

Peak 7

This peak is also present at relatively low abundance in the profile of serum from a patient with chronic hepatitis (third arrow in second panel of the left sequencing column in FIG. 5) and in normal serum (not shown). Its sequencing can most easily be followed in the third sequencing column, showing one of the most severely affected sera in our collection. Peak 7 is the third most abundant glycan in this profile and neither this peak, nor any of its digestion products, co-migrates with any of the reference glycans mentioned above or their digestion products. As no comigration is seen down to the quadruple exoglycosidase digest, this means that a substituent is present that is absent from these reference glycans. After the quadruple digest, the Peak 7 digestion product migrates one glucose unit slower than the trimannose core oligosaccharide, which means that a substituent is present on this trimannose core with a size of one monosaccharide. Taking into account the results of a 3D HPLC mapping study of total healthy serum glycoprotein N-glycans (Nakagawa H. et al. (1995) *Anal. Biochem.* 226, 130-138), this can only be a bisecting GlcNAc. This substituent is resistant to digestion with Jack Bean β-N-acetylhexosaminidase under the conditions used here. This statement is confirmed by the resistance to β-N-acetylhexosaminidase of the bisecting GlcNAc residue on a bisected biantennary core-fucosylated reference glycan, see FIG. 5, reference panel under the third sequencing column). Fucosidase digest induces a shift in the Peak 7 mobility of 1.2 glucose units, which signals the presence of a core-α-1,6-linked fucose residue. Supplementary β-1,4-galactosidase digestion shifts the peak another two glucose units, which indicates the presence of two β-1,4-galactose residues. Thus, we conclude that Peak 7 represents the bisected biantennary, bi-β-1,4-galactosylated, core-α-1,6-fucosylated glycan structure. This result is corroborated by the co-elution of all Peak 7's digestion products with the corresponding digestion products of the reference glycan with this structure (bottom panel of the third sequencing column in FIG. 5). This bisecting GlcNAc substituent is the product of N-acetylglucosaminyltransferase III (GnT-III) activity on the structure represented by Peak 6, the core-α-1,6-fucosylated variant of Peak 3 (The structure for Peak 6 was determined in the accompanying study (Callewaert, N. et al. (2003) *Glycobiology* 13, 367-375).

Peak 1

Peak 1 shifts 1.2 glucose units upon fucosidase digestion, to the position of the agalacto biantennary reference glycan (first peak in the reference panel at the bottom of the central sequencing column). Moreover, upon galactosidase digestion, the peak at this position becomes very intense because Peak 6 shifts to this position (structure of Peak 6: bigalacto core-fucosylated biantennary glycan). Taken together, these data demonstrate that Peak 1 is the biantennary, agalacto, core-α-1,6-fucosylated glycan. Its up-regulation in the HCC and/or cirrhosis sample group thus signals a combination of undergalactosylation and increased core fucosylation of the serum glycoproteins.

Peak 2

The identification of this peak is more difficult due to its relatively low abundance. Nevertheless, sufficient information can be derived to positively identify its structure: in the profile resulting from double digestion with sialidase and β-1,4-galactosidase, the product of Peak 7 exactly co-migrates with Peak 2 in the sialidase panel. Subsequently, as Peak 2 is not observed in the left sequencing column (hepatitis sample) at this scale, we can identify its exoglycosidase products in the sialidase+fucosidase double digestion pattern of the other two samples, where Peak 2 is detectable. No peak is present anymore at the position of Peak 2 upon fucosidase digestion, and there is only one new peak that can be the digestion product (highlighted in gray, first arrow in the sialidase+fucosidase profile of the middle sequencing column). In the triple digestion profile (supplementary β-1,4-galactosidase), this peak becomes more intense because the digestion product of Peak 7 comigrates with it. Supplementary digestion with hexosaminidase leaves no trace of a peak at this position. This leads us to the conclusion that Peak 2 represents the bisected, agalacto core-α-1,6-fucosylated structure. Thus, this peak bears a combination of the structural alterations of peak 3 and peak 7, i.e., it is nongalactosylated and it has a bisecting GlcNAc residue.

Peak 9 was assigned before (Callewaert, N. et al. (2003) *Glycobiology* 13, 367-375) and is a branch-fucosylated derivative of the triantennary trigalacto structure.

In summary, in liver cirrhosis, there is an increased abundance of undergalactosylated N-glycans (Peaks 1 and 2), an increase of N-glycans modified with a bisecting N-acetylglucosamine (GlcNAc) residue (Peaks 2 and 7) and a decrease of fully galactosylated bi-and triantennary N-glycans (Peaks 3 and 8).

10. Monitoring of Fibrosis with a Sialylated N-glycan Profile

Figure 9:
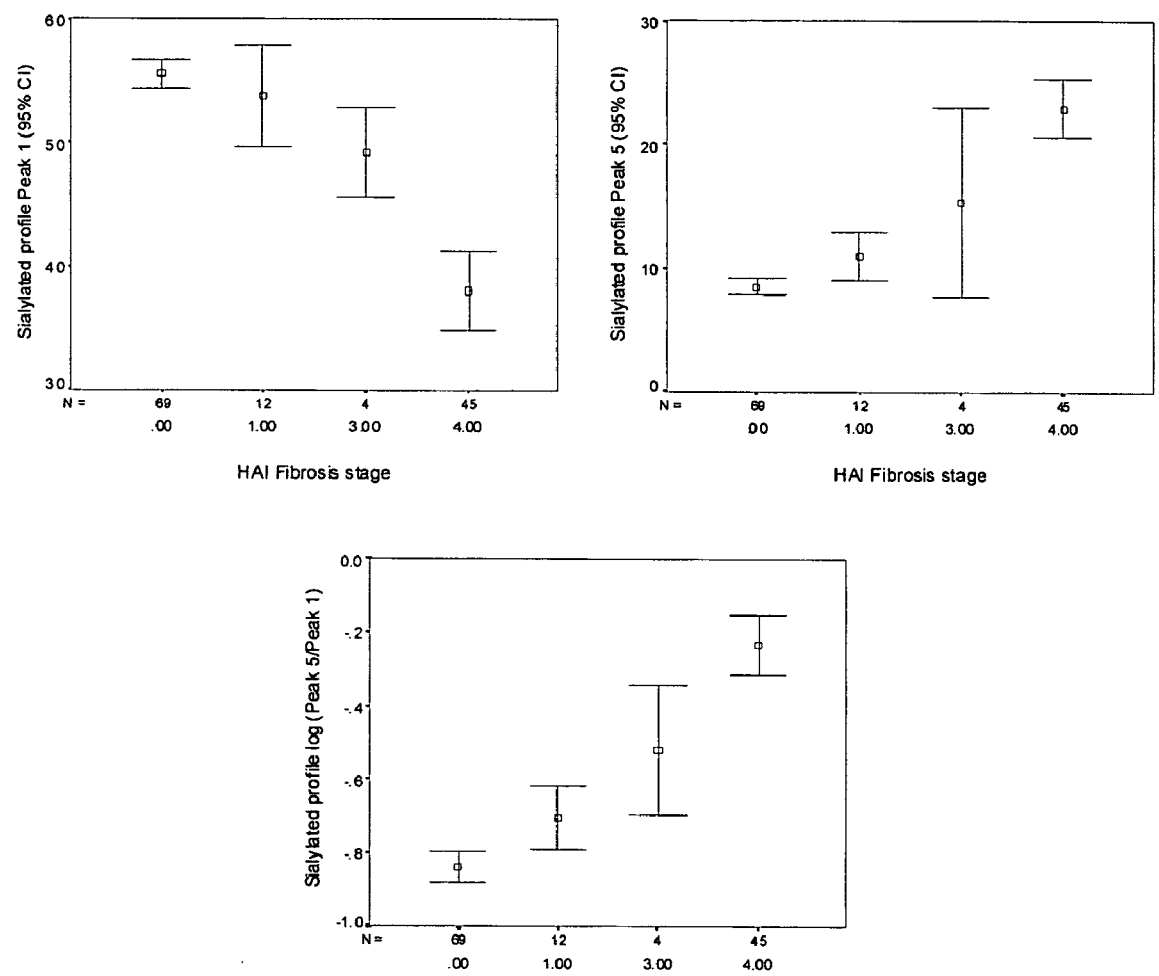
FIG. 9: Fibrosis marker derived from the sialylated N-glycan profile of total serum glycoproteins. The peak height of the seven major, well-resolved peaks present in all N-glycan profiles under study were quantified and normalized to the total abundance of quantified peaks in each profile. Peak 1 and Peak 5 correlated the best with the HAI fibrosis stages (assessed by Spearman rank correlation test, rho=−0.696 and 0.762, resp.). 95% confidence intervals are shown in Panels A, resp. B. Moreover, the peak heights of Peak 1 and Peak 5 correlate well with each other (Pearson r=−0.827). Consequently, we calculated the ratio between both peaks and log-transformed this value to normalize the distributions. This makes the test more simple, as only two Peaks need to be quantified instead of the whole profile. The 95% confidence intervals for the derived parameter log (sia 5 to sia 1). Are shown in Panel C. This parameter correlates well with the HAI fibrosis stages (Spearman rho=0.765). Sia 5 and sia 1 refer to the sialylated glycan peaks 1 and 5. Peak 5 in the sialylated profile has the same structure as in peak 1 of the desialylated profile (see, Example 9). Peak 1 in the sialylated profile has the same structure as peak 3 in the desialylated profile (see, Example 9). Note that sialylated structures have two additional alpha-2,6-N-acetylneuraminic acids when compared to desialylated structures.

Sialylated N-glycan profiles of the total protein mixture present in 131 serum samples were obtained. Sixty samples were provided by healthy blood donors, negative for HBV and HCV. This group was presumed to have no significant liver fibrosis (HAI fibrosis grade 0), which potentially is a slight under-estimation. Twelve patients were histologically determined to have only portal fibrosis without bridging (HAI fibrosis grade 1). Four patients had bridging fibrosis (HAI fibrosis grade 3), and 45 patients had fibrosis (HAI fibrosis grade 4). A detailed explanation of this experiment can be found in the legend of FIG. 9. The processing of N-glycans is as described in Materials and Methods except that a sialidase digestion was omitted.

Materials and Methods

1. Serum Samples and Clinical Diagnosis

The clinical study was approved by the local ethical committee of Ghent University Hospital. Informed consent was obtained from all the serum donors. A detailed characterization of the patients and the clinical diagnostic procedures that were followed can be found in Example 7.

2. Serum Protein N-glycome Sample Processing

The N-glycans present on the proteins in 5 µl of the sera (a total of 248) were released after protein binding to an Immobilon P-lined 96-well plate, derivatized with 8-aminopyrene-1,3,6-trisulfonic acid, desialylated and analyzed on an ABI 377A DNA sequencer[5] (Applied Biosystems, Foster City, Calif.). The protocol optimized for glycan release and labeling using a PCR thermocycler is as follows: 1 µl of a 10% SDS-containing 20 mM NH$_4$Ac buffer, pH=7 was added to 5 µl serum in PCR tubes. The tubes were heated at 95° C. for five minutes in a standard PCR thermocycler with heated lid. After cooling, 1 µl of 10% NP-40 solution was added to neutralize the denaturing effect of SDS on peptide N-glycosidase F (PNGase F, Glyko, Novato, Calif.). After the addition of 1 IUBMB mU of PNGase F, we closed the tubes and incubated them in the thermocycler at 37° C. for three hours. Subsequently, we added 8 µl of 50 mM NaAc, pH 5.0, followed by 2 µU *A. ureafaciens* sialidase (Glyko, Novato, Calif.) and incubated the tubes in the thermocycler at 37° C. for three hours. One µl of the resulting solution was transferred to a new PCR tube and evaporated to dryness with the thermocycler open at 65° C. and the tubes open. This evaporation is complete within five minutes, after which 1.5 µl of the labeling solution[5] was then added to the bottom of the tubes. The tightly closed tubes were then heated at 90° C. for one hour. (The elevated temperature ensures fast reaction kinetics.) 150 µl of water was added to every tube to stop the reaction and to dilute the label to about 100 pmol/µl. The resulting solution was used for analysis on the ABI 377 as described above or on the ABI 310 equipped with standard 47 cm ABI DNA-analysis capillaries according to the following specifications: as separation matrix, we used a 1:3 dilution of the proprietary POP6 polymer in Genetic Analyzer buffer (all materials from Applied Biosystems). The injection mixtures were prepared by 1:25 dilution of the APTS-derived serum glycan solutions (see, previous paragraph) in deionized formamide. Injection was for five seconds at 15 kV, followed by separation for 18 minutes at 15 kV and 30° C. As an internal standard, the rhodamine-labeled Genescan 2500 (ABI) reference ladder was used in the dilution specified by the manufacturer. No alterations of the sequencer hardware or software (see, below) are needed to perform these analyses, except for the coupling to an external cooling bath to the ABI 377 as described before.[5]

3. Data Processing

Data analysis was performed using the Genescan 3.1 software (Applied Biosystems). We quantified the heights of the 14 peaks that were detectable in all samples to obtain a numerical description of the profiles and analyzed these data with SPSS 11.0 (SPSS Inc., Chicago, Ill.). The assumption of normality of the variables over the studied populations was assessed using the Kolmogorov-Smirnov test at the 0.05 significance level. One-way analysis of variance was followed by Tukey's Honestly Significant Difference tests at $\alpha_{FW}$=0.0001. We used Receiver Operating Characteristic (ROC) curve analysis in SPSS 11.0 to assess the classification efficiency of the potential diagnostic variables. The curves in FIG. 4 were obtained using the non-parametric Lowess-regression.

4. Partial Structural Analysis of the N-glycan Pool by Exoglycosidase Array Sequencing One µl batches of APTS-labeled N-glycans as obtained according to the procedure described above were subjected to digestion with different mixtures of exoglycosidases in 20 mM NaAc pH 5.0. The enzymes used were: *Arthrobacter ureafaciens* sialidase (2 U/ml, Glyko); *Diplococcus pneumoniae* β-1,4-galactosidase (1 U/ml, Boehringer, Mannheim, Germany); Jack bean β-N-acetylhexosaminidase (30 U/ml, Glyko) and bovine epididymis α-fucosidase (0.5 U/ml, Glyko). Unit definitions are as specified by the enzyme suppliers. After completion of the digestions, the samples were evaporated to dryness, reconstituted in 1 µl water and analyzed on an ABI377 as described above.

REFERENCES

1. Staudt L. M. Molecular diagnosis of the hematologic cancers. *N. Engl. J. Med.* 348, 1777-1785 (2003).
2. Wulfkuhle J. D., L. A. Liotta and E. F. Petricoin. Proteomic applications for the early detection of cancer. *Nat. Rev. Cancer* 3, 267-275 (2003).
3. Hanash S. Disease proteomics. *Nature* 422, 226-232 (2003).
4. Brindle J. T. et al. Rapid and noninvasive diagnosis of the presence and severity of coronary heart disease using $^1$H-NMR-based metabonomics. *Nat. Med.* 8, 1439-1444 (2002).
5. Callewaert N., S. Geysens, F. Molemans and R. Contreras. Ultrasensitive profiling and sequencing of N-linked oligosaccharides using standard DNA-sequencing equipment. *Glycobiology* 11, 275-281 (2001).
6. Opanasopit P. et al. In vivo recognition of mannosylated proteins by hepatic mannose receptors and mannan-binding protein. *Am. J. Physiol. Gastrointest. Liver Physiol.* 280, G879-889 (2001).
7. Lee S. J. et al. Mannose receptor-mediated regulation of serum glycoprotein homeostasis. *Science* 295, 1898-1901 (2002).
8. Ashwell G. and J. Harford. Carbohydrate-specific receptors of the liver. *Annu. Rev. Biochem.* 51, 531-554 (1982).
9. Parekh R. B. et al. Association of rheumatoid arthritis and primary osteoarthritis with changes in the glycosylation pattern of total serum IgG. *Nature* 316, 452-7 (1985).
10. Cadranel J. F., P. Rufat and F. Degos. Practices of liver biopsy in France: results of a prospective nationwide survey. *Hepatology* 32, 477-481 (2000).
11. Menon K. V. and P. S. Kamath. Managing the complications of cirrhosis. *Mayo Clin. Proc.* 75, 501-509 (2000).
12. Kuper H. et al. The risk of liver and bile duct cancer in patients with chronic viral hepatitis, alcoholism, or cirrhosis. *Hepatology* 34, 714-718 (2001).
13. Piccinino F., E. Sagnelli, G. Pasquale and G. Giusti. Complications following percutaneous liver biopsy. A multicentre retrospective study on 68,276 biopsies. *J. Hepatol.* 2, 165-173 (1986).
14. Imbert-Bismut F. et al. Biochemical markers of liver fibrosis in patients with hepatitis C virus infection: a prospective study. *Lancet* 357, 1069-1075 (2001).
15. Poynard T. et al. Biochemical markers of liver fibrosis in patients infected by hepatitis C virus: longitudinal validation in a randomized trial. *J. Viral. Hepat.* 9, 128-133 (2002).

16. Henderson A. R. Assessing test accuracy and its clinical consequences: a primer for receiver operating characteristic curve analysis. *Ann. Clin. Biochem.* 30, 521-539 (1993).
17. Noe D. A. Selecting a diagnostic study's cutoff value by using its receiver operating characteristic curve. *Clin. Chem.* 29, 571-572 (1983).
18. The METAVIR cooperative group. Inter-and intra-observer variation in the assessment of liver biopsy of chronic hepatitis C. *Hepatology* 20, 15-20 (1994).
19. Bellentani S. et al. Prevalence of chronic liver disease in the general population of northern Italy: the Dionysos Study. *Hepatology* 20, 1442-1449 (1994).
20. Parekh R. B. et al. Association of rheumatoid arthritis and primary osteoarthritis with changes in the glycosylation pattern of total serum IgG. *Nature* 316, 452-7 (1985).
21. Stibler H. Carbohydrate-deficient transferrin in serum: a new marker of potentially harmful alcohol consumption reviewed. *Clin. Chem.* 37, 2029-37 (1991).
22. Nakagawa H. et al. Identification of neutral and sialyl N-linked oligosaccharide structures from human serum glycoproteins using three kinds of high-performance liquid chromatography. *Anal. Biochem.* 226, 130-138 (1995).
23. Miyoshi E. et al. Gene expression of N-acetylglucosaminyltransferases III and V: a possible implication for liver regeneration. *Hepatology* 22, 1847-1855 (1995).
24. Ishibashi K. et al. N-Acetylglucosaminyltransferase-III in human serum, and liver and hepatoma tissues—increased activity in liver cirrhosis and hepatoma patients. *Clin. Chim. Acta* 185, 325-332 (1989).
25. Sawamura T. et al. Hyperasialoglycoproteinemia in patients with chronic liver diseases and/or liver cell carcinoma. Asialoglycoprotein receptor in cirrhosis and liver cell carcinoma. *Gastroenterology* 87, 1217-1221 (1984).
26. Ise H., N. Sugihara, N. Negishi, T. Nikaido and T. Akaike. Low asialoglycoprotein receptor expression as markers for highly proliferative potential hepatocytes. *Biochem. Biophys. Res. Commun.* 285, 172-182 (2001).
27. Poynard T. et al. Impact of pegylated interferon alfa-2b and ribavirin on liver fibrosis in patients with chronic hepatitis C. *Gastroenterology* 122, 1303-1313 (2002).

What is claimed is:

1. A method of detecting liver disease characterized by the growth of scar tissue between areas of functional liver tissue or a change in the gradation of liver disease characterized by the growth of scar tissue between areas of functional liver tissue in a mammal, said method comprising:
   a) obtaining a sample of serum or blood plasma from the mammal, said sample representing a total mixture of serum or plasma proteins;
   b) generating a first profile of N-linked carbohydrates or fragments derived therefrom, or labeled derivatives of said N-linked carbohydrates or said N-linked carbohydrate fragments, or features of said N-linked carbohydrates or said N-linked carbohydrate fragments that are determined by the structure of said N-linked carbohydrates or said N-linked carbohydrate fragments; said N-linked carbohydrates or said N-linked fragments being obtained from the total mixture of serum or plasma proteins present in the serum or plasma sample from said mammal, wherein said first profile represents the diversity and concentration of N-linked carbohydrate moieties of the total mixture of serum or plasma proteins in said sample,
   c) measuring in the first profile an amount of at least one N-linked carbohydrate or N-linked carbohydrate fragment or a labeled derivative of said N-linked carbohydrate or said carbohydrate fragment, or a feature of at least one N-linked carbohydrate or N-linked carbohydrate fragment present in said N-linked carbohydrate profile,
   d) comparing the measured amount obtained in step c) with the quantified amount of said same at least one N-linked carbohydrate or N-linked carbohydrate fragment or said same at least one labeled derivative of said N-linked carbohydrate or said carbohydrate fragment, or said same at least one feature of said N-linked carbohydrate or N-linked carbohydrate fragment obtained from profiles derived from mammals free of said liver disease in order to detect either liver disease characterized by the growth of scar tissue between areas of functional liver tissue or, in the gradation of liver disease characterized by the growth of scar tissue between areas of functional liver tissue, wherein said profiles derived from mammals free of said liver disease represent the diversity and concentration of carbohydrate moieties of the total mixture of serum or plasma proteins of said mammals, and
   e) attributing the results of the comparison obtained in step d) to detect said liver disease or a change in the gradation of said liver disease in said mammal of step a).

2. The method according to claim 1 wherein said at least one N-linked carbohydrate is selected from the group consisting of:
   i) GlcNAc($\beta$-1,2)Man($\alpha$-1,3)[GlcNAc($\beta$-1,2)Man($\alpha$-1,6)]Man($\beta$-1,4)GlcNAc ($\beta$-1,4)[Fuc($\alpha$-1,6)]GlcNAc (glycan 1),
   ii) GlcNAc($\beta$-1,2)Man($\alpha$-1,3)[GlcNAc($\beta$-1,4)][GlcNAc ($\beta$-1,2)Man($\alpha$-1,6)]Man ($\beta$-1,4)GlcNAc($\beta$-1,4)[Fuc($\alpha$-1,6)]GlcNAc(glycan 2),
   iii) Gal($\beta$-1,4)GlcNAc($\beta$-1,2)Man($\alpha$-1,3)[GlcNAc($\beta$-1,4)][Gal($\beta$-1,4)GlcNAc ($\beta$-1,2)Man($\alpha$-1,6)]Man($\beta$-1,4) GlcNAc($\beta$-1,4)[Fuc($\alpha$-1,6)]GlcNAc (glycan 7),
   iv) Gal($\beta$-1,4)GlcNAc($\beta$-1,2)[Gal($\beta$-1,4)GlcNAc($\beta$-1,4)] Man($\alpha$-1,3)[Gal($\beta$-1,4) GlcNAc($\beta$-1,2)Man($\alpha$-1,6)] Man($\beta$-1,4)GlcNAc($\beta$-1,4)GlcNAc (glycan 8),
   v) a fragment derived of glycan 1, 2, 7 or 8,
   vi) a sialylated derivative of glycan 1, 2, 7 or 8, and
   vii) a feature of glycan 1, 2, 7 or 8 or derivative or fragment thereof.

3. The method according to claim 2 wherein said amount is measured as a relative amount between glycan 1 and glycan 8 and/or glycan 2 and glycan 8 and/or glycan 7 and glycan 8 or a fragment, sialylated derivative or feature thereof.

4. The method according to claim 3 wherein the relative amount between glycan 2 and glycan 8 is used to measure a linear change in the gradation of said liver disease.

5. The method according to claim 2, wherein the mammal is a human.

6. The method according to claim 2, said method further comprising:
   measuring quantitative or qualitative assessments of the mammal's physical condition, such as clinical chemistry parameters.

7. The method according to claim 6, wherein said measuring of clinical chemistry parameters comprises a fibrotest.

8. The method according to claim 3, wherein the mammal is a human.

9. The method according to claim 4, wherein the mammal is a human.

10. The method according to claim 1, wherein the mammal is a human.

11. The method according to claim 1, further comprising:
    measuring quantitative or qualitative assessments of the mammal's physical condition, such as clinical chemistry parameters.

12. The method according to claim 11, wherein said measuring of clinical chemistry parameters comprises a fibrotest.

* * * * *